United States Patent
Sasikumar et al.

(10) Patent No.: US 10,106,581 B2
(45) Date of Patent: *Oct. 23, 2018

(54) CYCLIC PEPTIDOMIMETIC COMPOUNDS AS IMMUNOMODULATORS

(71) Applicants: Pottayil Govindan Nair Sasikumar, Bangalore (IN); Muralidhara Ramachandra, Bangalore (IN); Seetharamaiah Setty Sudarshan Naremaddepalli, Bangalore (IN)

(72) Inventors: Pottayil Govindan Nair Sasikumar, Bangalore (IN); Muralidhara Ramachandra, Bangalore (IN); Seetharamaiah Setty Sudarshan Naremaddepalli, Bangalore (IN)

(73) Assignee: Aurigene Discovery Technologies Limited, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/332,805

(22) Filed: Oct. 24, 2016

(65) Prior Publication Data
US 2017/0101444 A1   Apr. 13, 2017

Related U.S. Application Data

(60) Continuation of application No. 14/989,954, filed on Jan. 7, 2016, which is a division of application No. 14/478,806, filed on Sep. 5, 2014, now Pat. No. 9,233,940.

(51) Int. Cl.
C07K 7/64  (2006.01)
A61K 38/00  (2006.01)

(52) U.S. Cl.
CPC .............. C07K 7/64 (2013.01); *A61K 38/00* (2013.01)

(58) Field of Classification Search
CPC .................................................. C07K 7/64
See application file for complete search history.

(56) References Cited

U.S. PATENT DOCUMENTS 8,735,553 B1   5/2014   Li et al.

FOREIGN PATENT DOCUMENTS

| WO | 2001014557 A1 | 3/2001 |
| WO | 2002079499 A1 | 10/2002 |
| WO | 2002086083 A2 | 10/2002 |
| WO | 2003042402 A2 | 5/2003 |
| WO | 2004004771 A1 | 1/2004 |
| WO | 2004056875 A1 | 7/2004 |
| WO | 2006121168 A1 | 11/2006 |
| WO | 2008156712 A1 | 12/2008 |
| WO | 2010077634 A1 | 7/2010 |
| WO | 2011066389 A1 | 6/2011 |
| WO | 2011161699 A2 | 12/2011 |

(Continued)

OTHER PUBLICATIONS

Harvey Rd. Immunologic and Clinical Effects of Targeting PD-1 in Lung Cancer, Clinical Pharmacology & Therapeutics (2014) 96 (02) : 214-223.

(Continued)

*Primary Examiner* — Timothy P Thomas
(74) *Attorney, Agent, or Firm* — Benjamin Aaron Adler

(57) ABSTRACT

Methods of making a compound according to the following scheme:

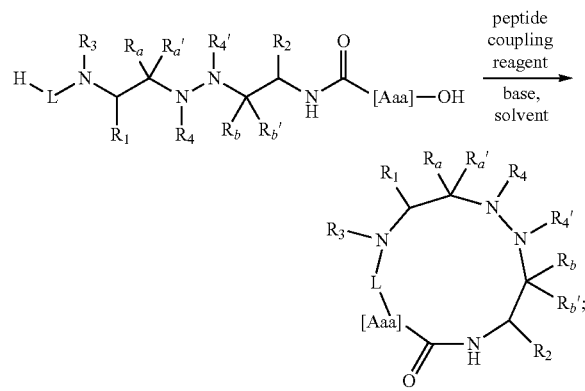

wherein:
$R_1$ is a side chain of an amino acid residue selected from Ala, Ser, Thr and Leu;
$R_2$ is a side chain of an amino acid residue selected from Asp, Glu, Gln and Asn;
[Aaa] is an amino acid residue selected from Ser, Asp, Ala, Ile, Phe, Trp, Lys, Glu and Thr;
$R_3$ is hydrogen or alkyl;
Each of $R_4$ and $R_4'$ independently is hydrogen or alkyl;
Both $R_a$ and $R_a'$ are hydrogen; or together are an oxo (=O) group;
Both $R_b$ and $R_b'$ are hydrogen; or together are an oxo (=O) group;
L is

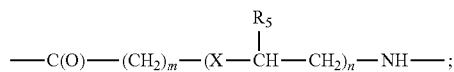

X is $CH_2$, O or S;
$R_5$ is hydrogen or alkyl;
m is an integer from 1 to 3; and
n is an integer from 2 to 20.

6 Claims, 7 Drawing Sheets

(56) References Cited

FOREIGN PATENT DOCUMENTS

| | | |
|---|---|---|
| WO | 2012168944 A1 | 12/2012 |
| WO | 2013132317 A1 | 9/2013 |
| WO | 2013144704 A1 | 10/2013 |
| WO | 2013170066 A1 | 11/2013 |
| WO | 2014055897 A2 | 4/2014 |
| WO | 2014059173 A2 | 4/2014 |
| WO | 2014100079 A1 | 6/2014 |

OTHER PUBLICATIONS

Pedoeem, et al. Programmed death-1 pathway in cancer and autoimmunity, Clinical Immunology (2014) 153:145-152.

Shi et al. The role of PD-1 and PD-L1 in T-cell immune suppression in patients with hematological malignancies. Journal of Hematology & Oncology 2013, 6:74 p. 1-6.

Jin et al. Role of PD-1 in Regulating T-Cell Immunity. Current Topics in Microbiology and Immunology (2010) published online: Sep. 11, 2010 350: pp. 17-37.

CYCLIC PEPTIDOMIMETIC COMPOUNDS AS IMMUNOMODULATORS

CROSS-REFERENCE TO RELATED APPLICATIONS

This application is a continuation of pending application U.S. Ser. No. 14/989,954, filed Jan. 7, 2016, which is a divisional under 35 U.S.C. § 120 of U.S. Ser. No. 14/478, 806, filed Sep. 5, 2014, now U.S. Pat. No. 9,233,940, which claims benefit of priority under 35 U.S.C. § 119(a) of Indian provisional application number 4010/CHE/2013, filed Sep. 6, 2013, now abandoned, the contents of each of which is hereby incorporated by reference in its entirety.

BACKGROUND OF THE INVENTION

Technical Field of the Invention

The present invention relates to cyclic peptidomimetic compounds therapeutically useful as immune modulators. The invention also relates to pharmaceutical compositions comprising said cyclic peptidomimetic compounds as therapeutic agents.

Description of the Related Art

Programmed cell death-1 (PD-1) is a member of the CD28 superfamily that delivers negative signals upon interaction with its two ligands, PD-L1 or PD-L2. PD-1 and its ligands are broadly expressed and exert a wider range of immunoregulatory roles in T cells activation and tolerance compared with other CD28 members. PD-1 and its ligands are involved in attenuating infectious immunity and tumor immunity, and facilitating chronic infection and tumor progression. The biological significance of PD-1 and its ligand suggests the therapeutic potential of manipulation of PD-1 pathway against various human diseases (Ariel Pedoeem et al., Curr Top Microbiol Immunol. (2011); 350:17-37).

T-cell activation and dysfunction relies on direct and modulated receptors. Based on their functional outcome, co-signaling molecules can be divided as co-stimulators and co-inhibitors, which positively and negatively control the priming, growth, differentiation and functional maturation of a T-cell response (Li Shi, et al., Journal of Hematology & Oncology 2013, 6:74).

Therapeutic antibodies that block the programmed cell death protein-1 (PD-1) immune checkpoint pathway prevent T-cell down regulation and promote immune responses against cancer. Several PD-1 pathway inhibitors have shown robust activity in various phases of on-going clinical trials (RD Harvey, Clinical Pharmacology & Therapeutics (2014); 96 2, 214-223).

Programmed death-1 (PD-1) is a co-receptor that is expressed predominantly by T cells. The binding of PD-1 to its ligands, PD-L1 or PD-L2, is vital for the physiological regulation of the immune system. A major functional role of the PD-1 signaling pathway is the inhibition of self-reactive T cells, which serve to protect against autoimmune diseases. Elimination of the PD-1 pathway can therefore result in the breakdown of immune tolerance that can ultimately lead to the development of pathogenic autoimmunity. Conversely, tumor cells can at times co-opt the PD-1 pathway to escape from immunosurveillance mechanisms. Therefore, blockade of the PD-1 pathway has become an attractive target in cancer therapy. Current approaches include six agents that are either PD-1 and PD-L1 targeted neutralizing antibodies or fusion proteins. More than forty clinical trials are underway to better define the role of PD-1 blockade in variety of tumor types (Hyun-Tak Jin et al., Clinical Immunology (Amsterdam, Netherlands) (2014), 153(1), 145-152).

International applications WO 01/14557, WO 02/079499, WO 2002/086083, WO 03/042402, WO 2004/004771, WO 2004/056875, WO2006121168, WO2008156712, WO2010077634, WO2011066389, WO2014055897, WO2014059173, WO2014100079 and US patent U.S. Ser. No. 08/735,553 report PD-1 or PD-L1 inhibitory antibodies or fusion proteins.

Further, International applications, WO2011161699, WO2012/168944, WO2013144704 and WO2013132317 report peptides or peptidomimetic compounds which are capable of suppressing and/or inhibiting the programmed cell death 1 (PD1) signaling pathway.

Still there is a need for more potent, better and/or selective immune modulators of PD-1 pathway. The present invention provides cyclic peptidomimetic compounds which are capable of suppressing and/or inhibiting the programmed cell death 1 (PD1) signaling pathway.

SUMMARY OF THE INVENTION

In accordance with the present invention, cyclic peptidomimetic compounds or a stereoisomer thereof or a pharmaceutically acceptable salt thereof or pharmaceutical compositions thereof are provided which suppress and/or inhibit the programmed cell death 1 (PD1) signalling pathway.

In one aspect, the present invention provides cyclic peptidomimetic compounds of formula (I):

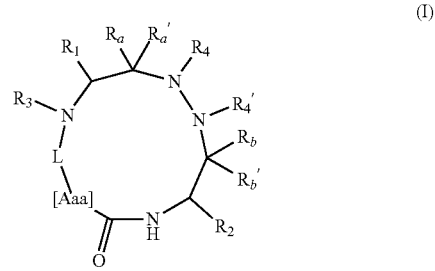

or a pharmaceutically acceptable salt or a stereoisomer thereof;
wherein,
$R_1$ is a side chain of amino acid Ala, Ser, Thr or Leu;
$R_2$ is a side chain of amino acid Asp, Glu, Gln or Asn;
[Aaa] is an amino acid residue selected from Ser, Asp, Ala, Ile, Phe, Trp, Lys, Glu or Thr;
$R_3$ is hydrogen or alkyl;
each of $R_4$ and $R_4'$ independently are hydrogen or alkyl;
both $R_a$ and $R_a'$ are hydrogen; or together are an oxo (=O) group;
both $R_b$ and $R_b'$ are hydrogen; or together are an oxo (=O) group;
L is

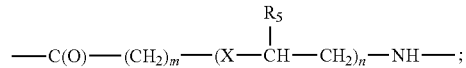

X is $CH_2$, O or S;
$R_5$ is hydrogen or alkyl;
m is an integer from 1 to 3; and
n is an integer from 2 to 20.

In a further aspect of the present invention, there is provided a pharmaceutical composition comprising a compound of formula (I) or a pharmaceutically acceptable salt or a stereoisomer and processes for preparing thereof.

In yet another aspect of the present invention, there is provided methods for suppressing and/or inhibiting the programmed cell death 1 (PD1) signaling pathway in a subject by administering cyclic peptidomimetic compounds of formula (I) or a pharmaceutically acceptable salt or a stereoisomer thereof or pharmaceutical compositions thereof.

In yet another aspect of the present invention, there is provided methods for inhibiting growth of tumour cells and/or metastasis in a subject by administering cyclic peptidomimetic compounds of formula (I) or a pharmaceutically acceptable salt or a stereoisomer thereof or pharmaceutical compositions thereof.

In yet another aspect of the present invention, there is provided methods for treating an infectious disease or a bacterial, viral and fungal infections in a subject by administering cyclic peptidomimetic compounds of formula (I) or a pharmaceutically acceptable salt or a stereoisomer thereof or pharmaceutical compositions thereof.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
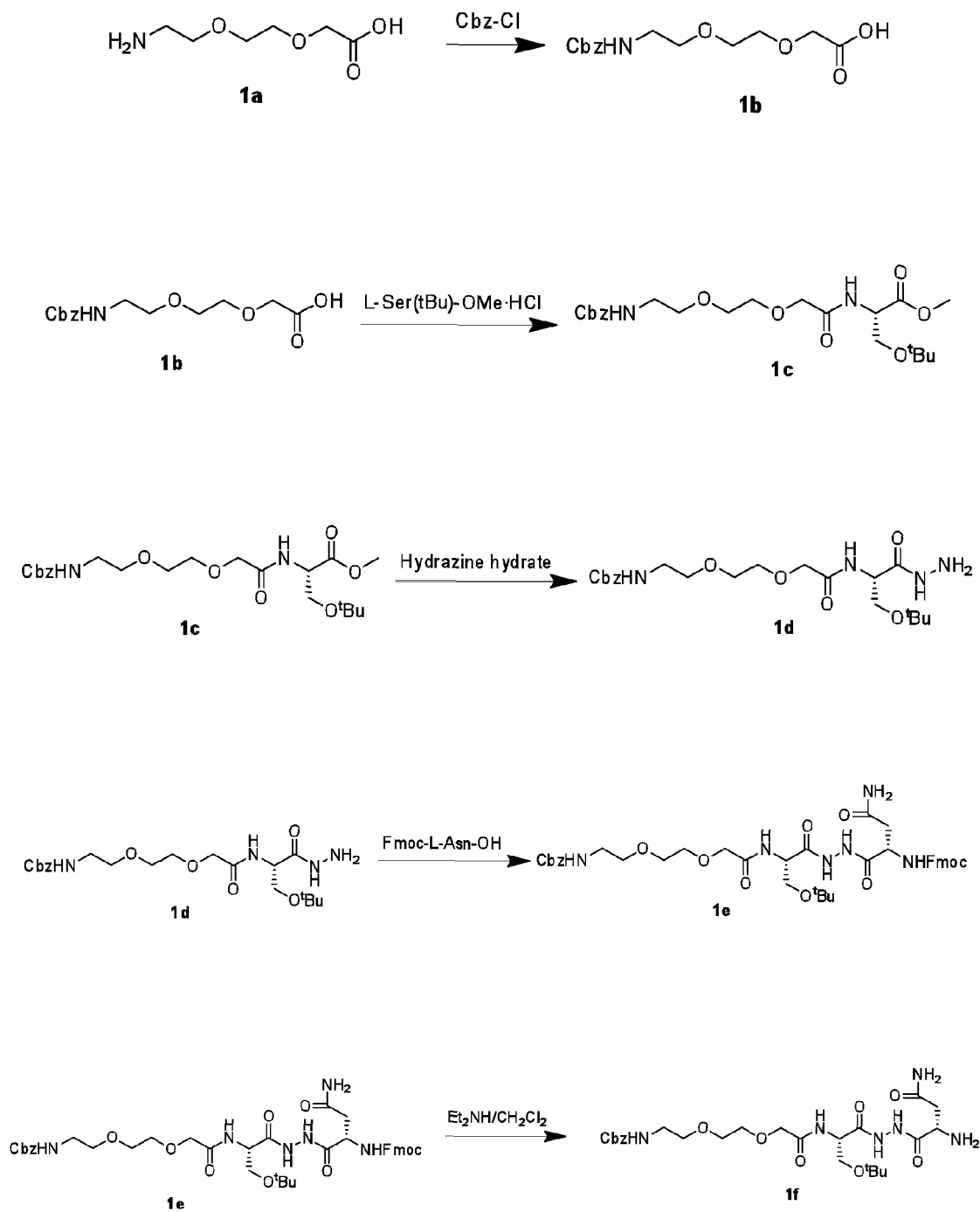
FIGS. 1A-1C depict the chemical synthetic scheme for Compound 1.

The present invention provides cyclic peptidomimetic compounds as therapeutic agents useful for treatment of disorders via immunopotentiation comprising inhibition of immunosuppressive signal induced due to PD-1, PD-L1, or PD-L2 and therapies using them.

Each embodiment is provided by way of explanation of the invention, and not by way of limitation of the invention. In fact, it will be apparent to those skilled in the art that various modification and variations can be made in the present invention without departing from the scope or spirit of the invention. For instance, features illustrated or described as part of one embodiment can be used on another embodiment to yield a still further embodiment. Thus it is intended that the present invention cover such modifications and variations as come within the scope of the appended claims and their equivalents. Other objects, features, and aspects of the present invention are disclosed in, or are obvious from, the following detailed description. It is to be understood by one of ordinary skill in the art that the present discussion is a description of exemplary embodiments only, and is not to be construed as limiting the broader aspects of the present invention.

In one embodiment, the present invention relates to compounds of formula (I)

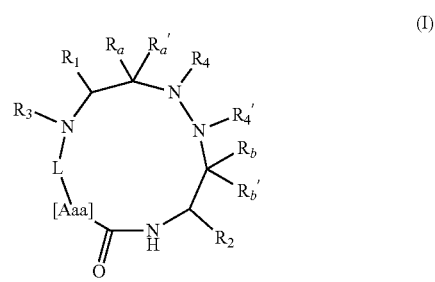

(I)

or a stereoisomer or a pharmaceutically acceptable salt thereof;
wherein;
$R_1$ is side chain of amino acid Ala, Ser, Thr or Leu;
$R_2$ is a side chain of amino acid Asp, Glu, Gln or Asn;
[Aaa] is an amino acid residue Ser, Asp, Ala, Ile, Phe, Trp, Lys, Glu, or Thr;
$R_3$ is hydrogen or alkyl;
each of $R_4$ and $R_4'$ independently are hydrogen or alkyl;
both $R_a$ and $R_a'$ are hydrogen; or together are an oxo (=O) group;
both $R_b$ and $R_b'$ are hydrogen; or together are an oxo (=O) group;
L is

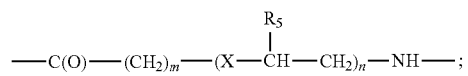

X is $CH_2$, O or S;
$R_5$ is hydrogen or alkyl;
m is an integer from 1 to 3; and
n is an integer from 2 to 20.

In a particular embodiment of the compounds of formula (I), the invention comprises a particular series of compounds of formula (IA):

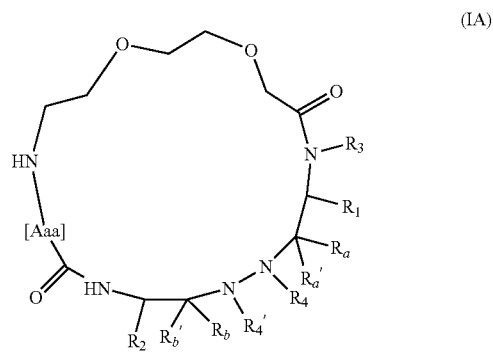

(IA)

wherein, $R_1$, $R_2$, $R_3$, $R_4$, $R_4'$, $R_a$, $R_a'$, $R_b$, $R_b'$ and [Aaa] are same as defined in formula (I).

In a particular embodiment of the compounds of formula (I), the invention comprises a particular series of compounds of formula (IB):

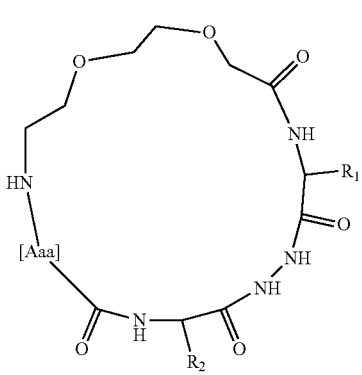

(IB)

wherein, $R_1$, $R_2$ and [Aaa] are same as defined in formula (I).

In yet another embodiment of the compounds of formula (I), the invention comprises a particular series of compounds of formula (IC):

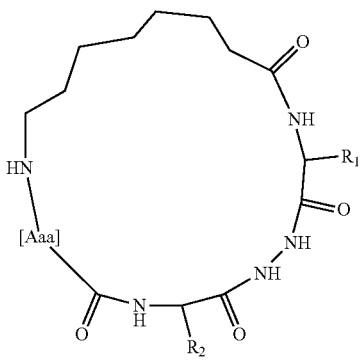

(IC)

wherein, $R_1$, $R_2$ and [Aaa] are same as defined in formula (I).

In yet another embodiment, the present invention provides compounds of formula (I), wherein,
$R_1$ is a side chain of amino acid Ser or Thr;
$R_2$ is a side chain of amino acid of Asp, Asn or Glu;
[Aaa] is an amino acid residue selected from Ser or Thr;
$R_3$, $R_4$ and $R_4'$ independently are hydrogen;
both $R_a$ and $R_a'$ together are an oxo (=O) group;
both $R_b$ and $R_b'$ together are an oxo (=O) group;
L is —C(O)—$(CH_2)_m$—(X—$CH_2$—$CH_2)_n$—NH—;
X is $CH_2$ or O;
m is an integer from 1 to 3; and
n is an integer from 2 to 20;
or a pharmaceutically acceptable salt or a stereoisomer thereof.

The embodiments below are illustrative of the present invention and are not intended to limit the claims to the specific embodiments exemplified.

In one embodiment, specifically provided are compounds of the formula (I), in which L is

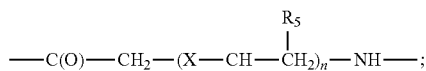

wherein X, n and $R_5$ are the same as defined in formula (I).

In another embodiment, specifically provided are compounds of the formula (I), in which L is

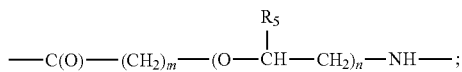

is wherein m, n and $R_5$ are the same as defined in formula (I).

In yet another embodiment, specifically provided are the compounds of the formula (I), in which L is —C(O)—$(CH_2)_m$—(X—$CH_2$—$CH_2)_n$—NH—; wherein m, n and X are the same as defined in formula (I).

In yet another embodiment, specifically provided are compounds of the formula (I), in which L is

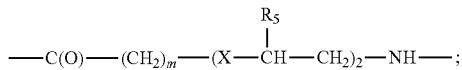

wherein m, X and $R_5$ are the same as defined in formula (I).

In yet another embodiment, specifically provided are compounds of the formula (I), in which L is —C(O)—$CH_2$—$(OCH_2CH_2)_2$—NH—.

In another embodiment, specifically provided are compounds of the formula (I), (IA), (IB) and (IC), in which $R_1$ is side chain of Ser.

In yet another embodiment, specifically provided are compounds of the formula (I), (IA), (IB) and (IC) in which $R_1$ is side chain of Thr.

In yet another embodiment, specifically provided are compounds of the formula (I), (IA) and (IB), in which $R_2$ is side chain of Asp.

In yet another embodiment, specifically provided are compounds of the formula (I), (IA), (IB) and (IC) in which $R_2$ is side chain of Asn.

In yet another embodiment, specifically provided are compounds of the formula (I), (IA), (IB) and (IC) in which $R_2$ is side chain of Glu.

In yet another embodiment, specifically provided are compounds of the formula (I), (IA), (IB) and (IC) in which [Aaa] is Ser.

In yet another embodiment, specifically provided are compounds of the formula (I), (IA), (IB) and (IC) in which [Aaa] is Thr.

In yet another embodiment, specifically provided are compounds of the formula (I), (IA) and (IB) in which [Aaa] is Asp.

In yet another embodiment, specifically provided are compounds of the formula (I), (IA) and (IB) in which [Aaa] is Lys or Ile.

In yet another embodiment, specifically provided are compounds of the formula (I), (IA) and (IB), in which one, more or all amino acid/s is/are D amino acid/s.

In yet another embodiment, specifically provided are compounds of the formula (I) and (IA), in which $R_4'$ is $C_{1-5}$alkyl such as methyl.

In yet another embodiment, specifically provided are compounds of the formula (I) and (IA), in which $R_4$ is $C_{1-5}$ alkyl such as methyl.

In yet another embodiment, specifically provided are compounds of the formula (I) and (IA), in which both $R_a$ and $R_a'$ are hydrogen.

In yet another embodiment, specifically provided are compounds of the formula (I) and (IA), in which both $R_b$ and $R_b'$ are hydrogen.

In yet another embodiment, specifically provided are compounds of the formula (I) and (IA), in which both $R_a$ and $R_a'$ together represent an oxo (=O) group.

In yet another embodiment, specifically provided are compounds of the formula (I) and (IA), in which both $R_b$ and $R_b'$ together represent an oxo (=O) group.

In yet another embodiment, specifically provided are compounds of the formula (I) and (IA), in which both $R_4$ and $R_4'$ are hydrogen.

In yet another embodiment, specifically provided are compounds of the formula (I) and (IA), in which $R_3$ is hydrogen.

In an embodiment, specific compounds of formula (I) without any limitation are enumerated in Table (1):

TABLE 1

| Compound No. | Structure |
|---|---|
| 1 | 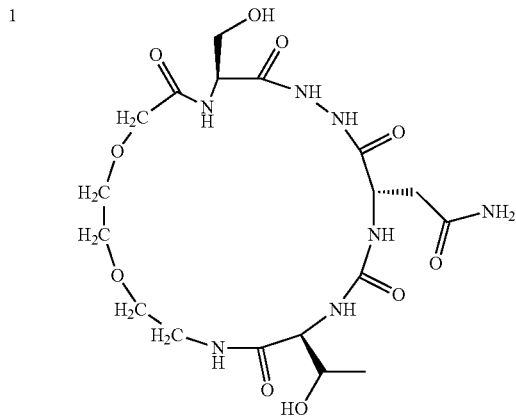 |
| 2 | 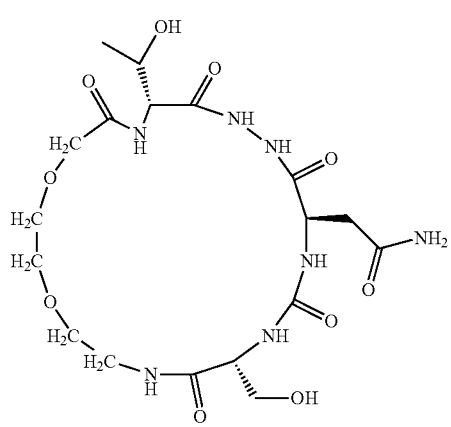 [SMILES: CC(O)[C@H]1NC(=O)COCCOCCNC(=O)[C@@H](CO)NC(=O)N[C@H](CC(N)=O)C(=O)NNC1=O] |

TABLE 1-continued

| Compound No. | Structure |
|---|---|
| 3 | 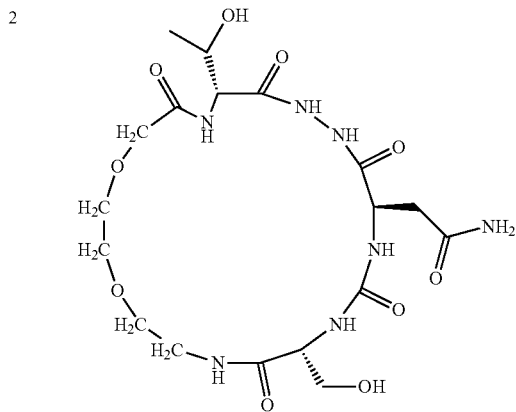 |
| 4 | 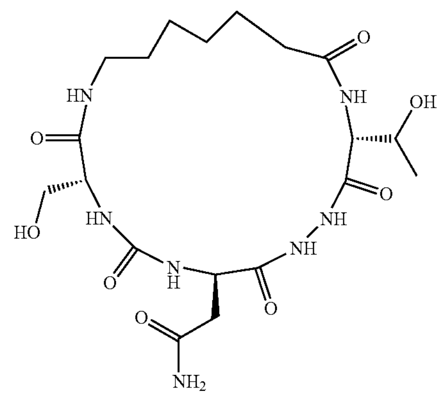 [SMILES: CC(O)[C@H]1NC(=O)CCCCCCNC(=O)[C@@H](CO)NC(=O)N[C@H](CC(N)=O)C(=O)NNC1=O] |
| 5 | 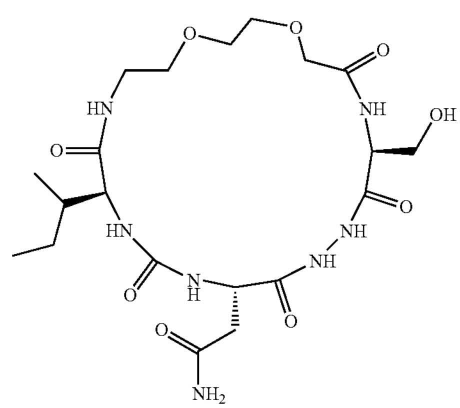 [SMILES: CCC(C)[C@@H]1NC(=O)N[C@@H](CC(N)=O)C(=O)NNC(=O)[C@H](CO)NC(=O)COCCOCCNC1=O] |

TABLE 1-continued
| Compound No. | Structure |
|---|---|
| 6 | 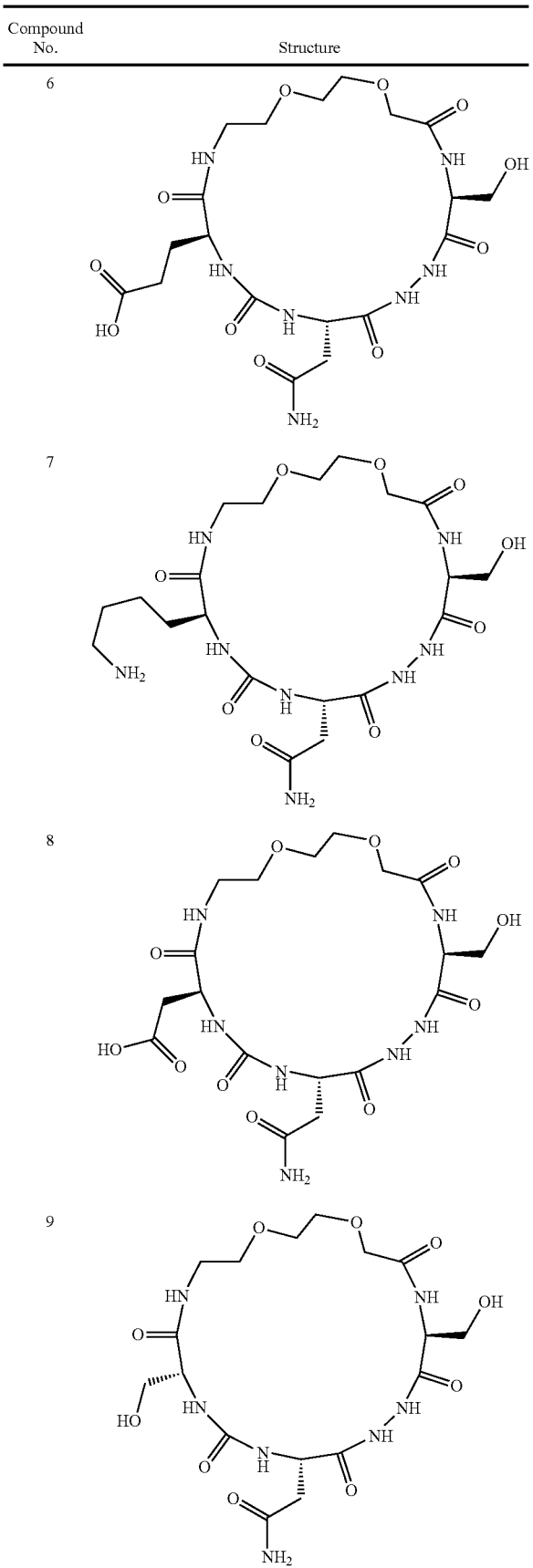 |
| 7 | 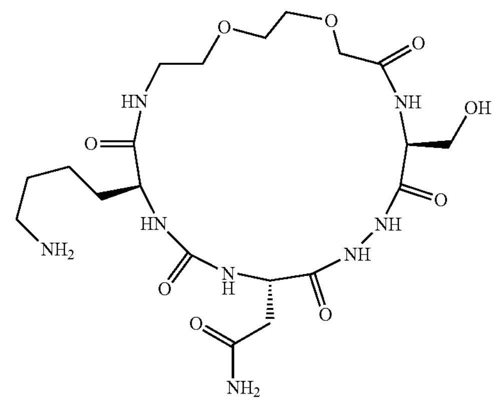 [SMILES: NCCCC[C@@H]1NC(=O)N[C@@H](CC(N)=O)C(=O)NNC(=O)[C@H](CO)NC(=O)COCCOCCNC1=O] |
| 8 | 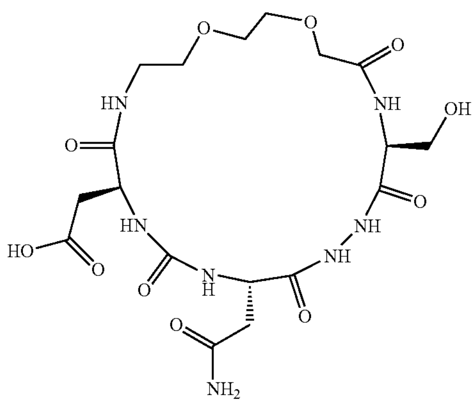 [SMILES: NC(=O)C[C@@H]1NC(=O)N[C@@H](CC(=O)O)C(=O)NCCOCCOCC(=O)N[C@@H](CO)C(=O)NNC1=O] |
| 9 | 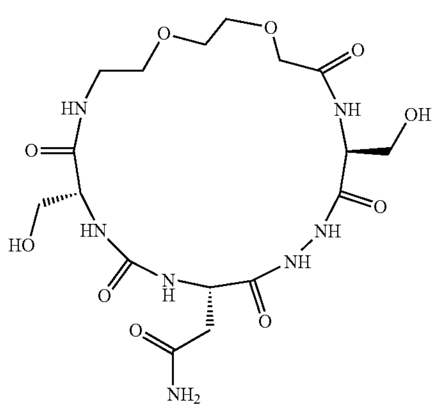 [SMILES: NC(=O)C[C@@H]1NC(=O)N[C@H](CO)C(=O)NCCOCCOCC(=O)N[C@@H](CO)C(=O)NNC1=O] |
| 10 | 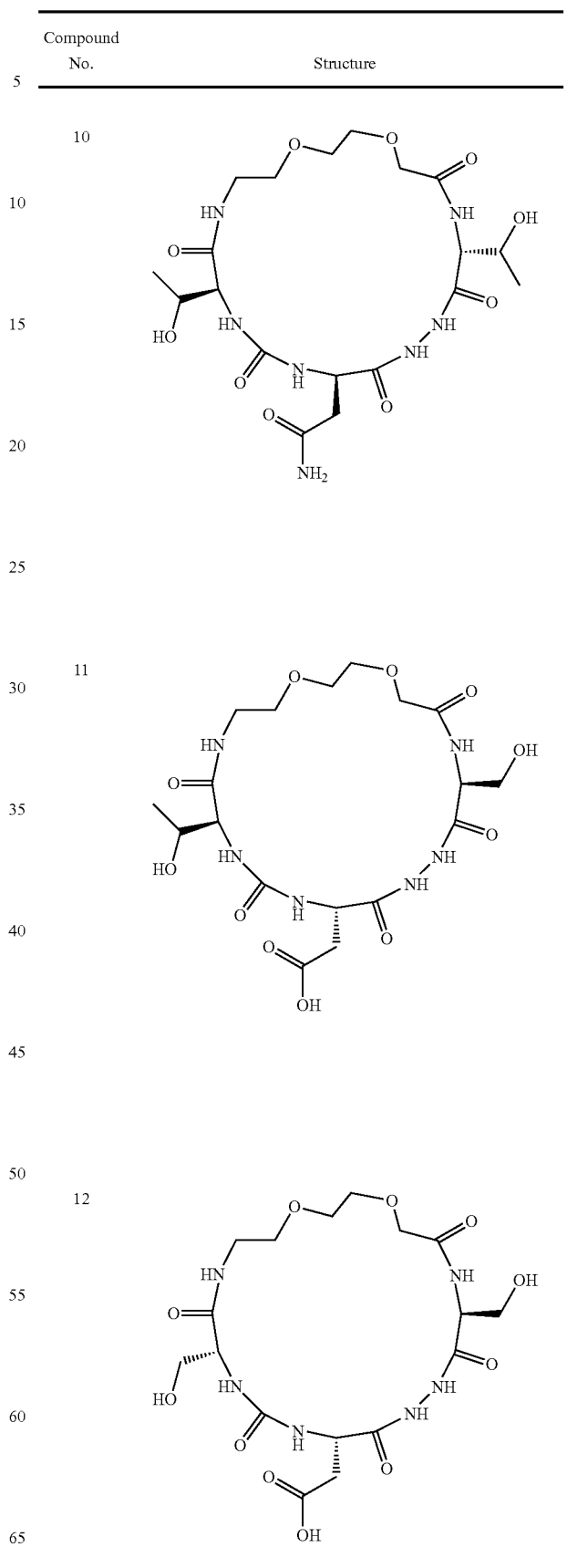 |
| 11 | |
| 12 | |

TABLE 1-continued

| Compound No. | Structure |
|---|---|
| 13 | (structure) |
| 14 | (structure) | or a pharmaceutically acceptable salt or a stereoisomer thereof thereof.

In one embodiment, the present invention provides a pharmaceutical composition comprising the compound as disclosed, and a pharmaceutically acceptable carrier or diluent.

In another embodiment, the pharmaceutical composition comprises at least one additional pharmaceutical agent wherein the additional pharmaceutical agent is an anticancer agent, chemotherapy agent, or antiproliferative compound.

The compounds as disclosed in the present invention are formulated for pharmaceutical administration.

In one embodiment, the present invention provides use of the compounds as disclosed in the present invention for the preparation of a medicament for the treatment of cancer.

In one embodiment, the present invention provides use of the compounds as disclosed in the present invention for the preparation of a medicament for the treatment of infectious diseases or bacterial, viral and fungal infections.

In one embodiment, the present invention provides a method of treatment of cancer, wherein the method comprises administration of an effective amount of the compound of the present invention or of a pharmaceutical composition thereof to the subject in need thereof.

In one embodiment, the present invention provides a method for inhibiting growth of tumour cells and/or metastasis by administering an effective amount of the compound of the present invention or of a pharmaceutical composition thereof to the subject in need thereof.

Representative tumour cells include cancer such as but not limited to melanoma, renal cancer, prostate cancer, breast cancer, colon cancer and lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), primary CNS lymphoma, tumour angiogenesis, spinal axis tumour, brain stem glioma, pituitary adenoma, Kaposi's sarcoma, epidermoid cancer, squamous cell cancer, T-cell lymphoma, environmentally induced cancers including those induced by asbestos, and combinations of said cancers.

Still yet another embodiment of the present invention provides a method of treatment of infection via immunopotentiation caused by inhibition of immunosuppressive signal induced by PD-1, PD-L1, or PD-L2, wherein the method comprises administration of an effective amount of the compound of the present invention or of a pharmaceutical composition thereof to the subject in need thereof.

The infectious disease includes but not limited to HIV, Influenza, Herpes, *Giardia*, Malaria, *Leishmania*, the pathogenic infection by the virus Hepatitis (A, B, & C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria chlamydia, rickettsial bacteria, mycobacteria, staphylococci, streptococci, pneumonococci, meningococci and conococci, *klebsiella, proteus, serratia, pseudomonas, E. coli, legionella, diphtheria, salmonella, bacilli*, cholera, tetanus, botulism, anthrax, plague, leptospirosis, and Lyme's disease bacteria, pathogenic infection by the fungi *Candida (albicans, krusei, glabrata, tropicalis*, etc.), *Cryptococcus neoformans, Aspergillus (fumigatus, niger*, etc.), Genus *Mucorales (mucor, absidia, rhizophus), Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*.

The compounds of the present invention may be used as single drugs or as a pharmaceutical composition in which the compound is mixed with various pharmacologically acceptable materials.

The pharmaceutical composition is usually administered by oral or inhalation routes, but can be administered by parenteral administration route. In the practice of this invention, compositions can be administered, for example, by orally, intravenous infusion, topically, intraperitoneally, intravesically or intrathecally. Examples of the parenteral administration includes but not limited to intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Oral administration, parenteral administration, subcutaneous administration and intravenous administration are the preferred methods of administration.

The dosage of the compounds of the present invention varies depending on age, weight, symptom, therapeutic efficacy, dosing regimen and/or treatment time. Generally, they may be administered by oral or inhalation routes, in an amount of 1 mg to 100 mg per time, from once a couple of days, once 3 days, once 2 days, once a day to a couple of times a day, in the case of an adult, or continuously administered by oral or inhalation routes from 1 to 24 hours a day. Since the dosage is affected by various conditions, an amount less than the above dosage may sometimes work well enough, or higher dosage may be required in some cases.

The compounds of the present invention may be administered in combination with other drugs for (1) complementation and/or enhancement of prevention and/or therapeutic efficacy of the preventive and/or therapeutic drug of the present invention, (2) dynamics, absorption improvement, dosage reduction of the preventive and/or therapeutic drug of the present invention, and/or (3) reduction of the side effects of the preventive and/or therapeutic drug of the present invention.

A concomitant medicine comprising the compounds of the present invention and other drug may be administered as a combination preparation in which both components are contained in a single formulation, or administered as separate formulations. The administration by separate formulations includes simultaneous administration and administration with some time intervals. In the case of the administration with some time intervals, the compound of the present invention can be administered first, followed by another drug or another drug can be administered first, followed by the compound of the present invention. The administration method of the respective drugs may be the same or different.

The dosage of the other drug can be properly selected, based on a dosage that has been clinically used. The compounding ratio of the compound of the present invention and the other drug can be properly selected according to age and weight of a subject to be administered, administration method, administration time, disorder to be treated, symptom and combination thereof. For example, the other drug may be used in an amount of 0.01 to 100 parts by mass, based on 1 part by mass of the compound of the present invention. The other drug may be a combination of two or more kind of arbitrary drugs in a proper proportion. The other drug that complements and/or enhances the preventive and/or therapeutic efficacy of the compound of the present invention includes not only those that have already been discovered, but those that will be discovered in future, based on the above mechanism.

Diseases on which this concomitant use exerts a preventive and/or therapeutic effect are not particularly limited. The concomitant medicine can be used for any diseases, as long as it complements and/or enhances the preventive and/or therapeutic efficacy of the compound of the present invention.

The compound of the present invention can be used with an existing chemotherapeutic concomitantly or in a mixture form. Examples of the chemotherapeutic include an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein inhibitor, platinum complex derivative, other immunotherapeutic drugs and other anticancer drugs. Further, it can be used with a cancer treatment adjunct, such as a leucopenia (neutropenia) treatment drug, thrombocytopenia treatment drug, antiemetic and cancer pain intervention drug, concomitantly or in a mixture form.

In one embodiment, the compound(s) of the present invention can be used with other immunomodulators and/or a potentiating agent concomitantly or in a mixture form. Examples of the immunomodulator include various cytokines, vaccines and adjuvants. Examples of these cytokines, vaccines and adjuvants that stimulates immune responses include but not limited to GM-CSF, M-CSF, G-CSF, interferon-$\alpha$, $\beta$, or $\gamma$, IL-1, IL-2, IL-3, IL-12, Poly (I:C) and $C_pG$.

In another embodiment, the potentiating agents includes cyclophosphamide and analogs of cyclophosphamide, anti-TGF$\beta$ and Imatinib (Gleevac), a mitosis inhibitor, such as paclitaxel, Sunitinib (Sutent) or other antiangiogenic agents, an aromatase inhibitor, such as letrozole, an A2a adenosine receptor (A2AR) antagonist, an angiogenesis inhibitor, anthracyclines, oxaliplatin, doxorubicin, TLR4 antagonists, and IL-18 antagonists.

Unless defined otherwise, all technical and scientific terms used herein have the same meaning as is commonly understood by one of skill in art to which the subject matter herein belongs. As used herein, the following definitions are supplied in order to facilitate the understanding of the present invention.

As used herein the term "alkyl" refers to a hydrocarbon chain radical that includes solely carbon and hydrogen atoms in the backbone, containing no unsaturation, having from one to twenty carbon atoms (i.e., $C_{1-20}$ alkyl) or one to ten carbon atoms (i.e., $C_{1-10}$ alkyl) or one to five carbon atoms (i.e., $C_{1-5}$ alkyl) and which is attached to the rest of the molecule by a single bond, e.g., including but not limited to methyl, ethyl, propyl, butyl, isobutyl, sec-butyl, tert-butyl, isopentyl or neopentyl. Unless set forth or recited to the contrary, all alkyl groups described or claimed herein may be straight chain or branched, substituted or unsubstituted.

As used herein, the term "amino acid" refers to amino acids having L or D stereochemistry at the alpha carbon.

As used herein, the term 'compound(s)' refers to the compounds disclosed in the present invention.

As used herein, the term "comprise" or "comprising" is generally used in the sense of include, that is to say permitting the presence of one or more features or components.

As used herein, the term "including" as well as other forms, such as "include", "includes," and "included," is not limiting.

"Pharmaceutically acceptable salt" is taken to mean an active ingredient, which comprises a compound of the formula (I) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "stereoisomer" refers to any enantiomers, diastereomers, or geometrical isomers of the compounds of formula (I), wherever they are chiral or when they bear one or more double bond. When the compounds of the formula (I) and related formulae are chiral, they can exist in racemic or in optically active form. Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis. In the case of racemic amines, diastereomers are formed from the mixture by reaction with an optically active resolving agent. Examples of suitable resolving agents are optically active acids such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel).

The term "subject" includes mammals (especially humans) and other animals, such as domestic animals (e.g., household pets including cats and dogs) and non-domestic animals (such as wildlife).

"Therapeutically effective amount" or "efficient amount" refers to sufficient amount of the compound(s) of the present invention that (i) treats or prevents the particular disease, disorder or syndrome (ii) attenuates, ameliorates or eliminates one or more symptoms of the particular disease, disorder or syndrome or (iii) prevents or delays the onset of one or more symptoms of the particular disease, disorder or syndrome described herein. In the case of cancer, the therapeutically effective amount of the drug may decrease the number of cancer cells; decrease the cancer size; inhibit (i.e., slow to some extent and alternatively stop) cancer cell infiltration into peripheral organs; suppress (i.e., slow to some extent and alternatively stop) tumor metastasis; inhibit, to some extent, tumor growth; and/or relieve to some extent one or more of the symptoms associated with the cancer. In the case of infectious disease states, the therapeutic effective amount is an amount sufficient to decrease or alleviate an infectious diseases, the symptoms of an infections caused by bacterial, viral and fungal.

Naturally-occurring amino acids are identified throughout the specification by the conventional three-letter abbreviations indicated in the below Table 2:

TABLE 2

| Name | 3-letter code |
|---|---|
| Alanine | Ala |
| Asparagine | Asn |

TABLE 2-continued

| Name | 3-letter code |
|---|---|
| Aspartic acid | Asp |
| Glutamic acid | Glu |
| Glutamine | Gln |
| Isoleucine | Ile |
| Leucine | Leu |
| Lysine | Lys |
| Phenylalanin | Phe |
| Serine | Ser |
| Threonine | Thr |
| Tryptophan | Trp |

The abbreviations used in the entire specification may be summarized herein below with their particular meaning.

° C. (degree Celsius); δ (delta); % (percentage); brine (NaCl solution); bs or brs (Broad singlet); Bzl (Benzyl); Cbz (Carboxybenzyl); Cbz-Cl (Benzyl chloroformate); $CH_2Cl_2$/DCM (Dichloromethane); $Cs_2CO_3$ (Cesium carbonate); DMF (Dimethyl formamide); DMSO (Dimethyl sulfoxide); DIPEA/DIEA (N, N-Diisopropyl ethylamine); DMSO-$d_6$ (Deuterated DMSO); d (Doublet); EtOAc (Ethyl acetate); $Et_2NH$ (Diethylamine); Fmoc (Fluorenylmethyloxycarbonyl); Fmoc-Cl (Fluorenylmethyloxycarbonyl chloride) g or gr (gram); H or $H_2$ (Hydrogen); $H_2O$ (Water); HOBt/HOBT (1-Hydroxy benzotriazole); HCl (Hydrochloric acid); h or hr (Hours); HATU (2-(1H-7-Azabenzotriazol-1-yl)-1,1,3,3-tetramethyl uranium hexafluoro phosphate methanaminium); Hz (Hertz); HPLC (High-performance liquid chromatography); LCMS (Liquid chromatography mass spectroscopy); MeOH/$CH_3OH$ (Methanol); mmol (Millimoles); M (Molar); μl/μL (Microliter); mL (Milliliter); mg (Milligram); min (minutes); m (Multiplet); mm (Millimeter); MHz (Megahertz); MS (ES) (Mass spectroscopy-electro spray); min (Minutes); Na (Sodium); NaOBu$^t$ (Sodium tert-butoxide); $NH_2NH_2.H_2O$ (Hydrazine hydrate); $Na_2SO_4$ (Sodium sulphate); $N_2$ (Nitrogen); NMR (Nuclear magnetic resonance spectroscopy); $NaHCO_3$ (Sodium bicarbonate); Pd—C(Palladiun on carbon); 10% Pd/C (10% palladium activated carbon); $Pd(OH)_2$ (palladium hydroxide); PD-L1 (Programmed death-ligand 1); PD-L2 (Programmed cell death 1 ligand 2); prep HPLC/prep-HPLC (Preparative High-performance liquid chromatography); PyBOP (Benzotriazol-1-yloxy)tripyrrolidinophosphonium hexafluorophosphate); RT/rt (room temperature); S (Singlet); $^t$Bu/tBu (Tertiary butyl) TEA/$Et_3N$ (Triethyl amine); TFA (Trifluoroaceticacid); TLC (Thin Layer Chromatography); THF (Tetrahydrofuran); TFA/$CF_3COOH$ (Trifluoro acetic acid); t (Triplet); $t_R$=(Retention time), etc.

An embodiment of the present invention provides the preparation of compounds of formula (I) according to the procedures of the following examples, using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present invention.

The starting materials are generally available from commercial sources such as Sigma-Aldrich, USA or Germany; Chem-Impex USA; G.L. Biochem, China and Spectrochem, India.

Purification and Characterization of Compounds

Analytical HPLC method: Analytical HPLC was performed using on ZIC HILIC 200 A° column (4.6 mm×250 mm, 5 μm), Flow rate: 1.0 mL/min. The elution conditions used are: Buffer A: 5 mmol ammonium acetate, Buffer B: Acetonitrile, Equilibration of the column with 90% buffer B and elution by a gradient of 90% to 40% buffer B during 30 min.

Preparative HPLC Method A: The crude material was purified by preparative HPLC using ZIC HILIC 200 A° column (21.2 mm×150 mm, 5 µm). The elution conditions used are Eluent: A: 5 mmol ammonium acetate B: Acetonitrile, Flow rate: 18 mL/min. The compound was eluted by gradient elution 0-3 min=90% buffer B, 3-20 min=90-40% buffer B with a flow rate of 20 mL/min.

Preparative HPLC Method B: Prep HPLC was performed using on ZIC HILIC 200 A° column (10 mm×250 mm, 5 µm), Flow rate: 5.0 mL/min. The elution conditions used are: Buffer A: 5 mmol ammonium acetate, Buffer B: Acetonitrile, Equilibration of the column with 90% buffer B and elution by a gradient of 90% to 40% buffer B during 20 min. LCMS was performed on AP1 2000 LC/MS/MS triple quad (Applied biosystems) with Agilent 1100 series HPLC with G1315 B DAD, using Mercury MS column or using Agilent LC/MSD VL single quad with Agilent 1100 series HPLC with G1315 B DAD, using Mercury MS column or using Shimadzu LCMS 2020 single quad with Prominence UFLC system with SPD-20 A DAD.

EXAMPLE 1

Synthesis of Compound 1

Figure 1B:
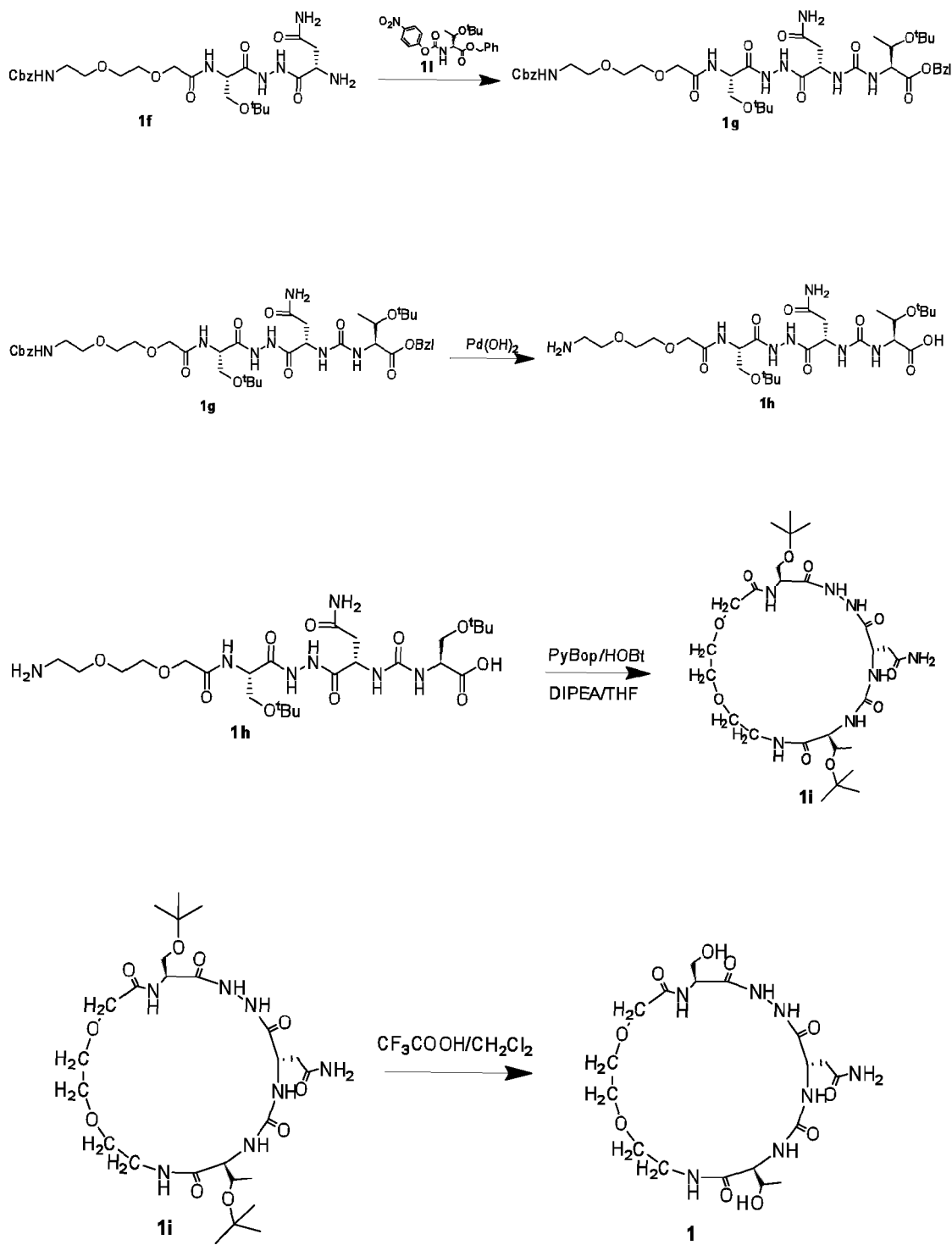
Figure 1C:
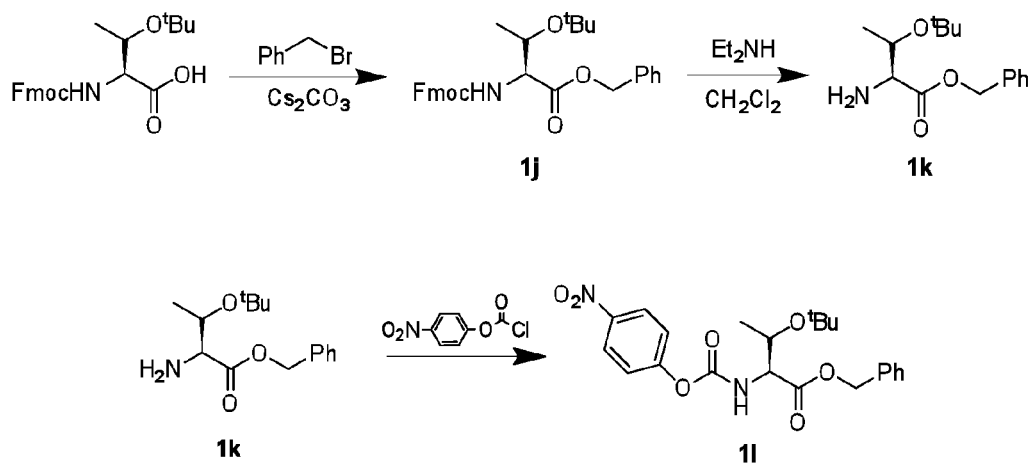

FIGS. 1A-1C illustrate Steps 1a to 1c.

Step 1a: Sodium hydroxide (12.2 g, 305 mmol) and Cbz-Cl (12.5 g, 73 mmol) were added to a solution of compound 1a (10.0 g, 61 mmol) in water (100 mL) and stirred at room temperature for 3 h. The completeness of the reaction was confirmed by TLC analysis. The reaction mass was partitioned between citric acid solution and ethyl acetate. Organic layer was washed with water, brine, dried over $Na_2SO_4$ and evaporated under reduced pressure to yield 11 g of compound 1b (Yield: 61.1%). LCMS: 298.0 $(M+H)^+$.

Step 1b: DIPEA (3.5 g, 26.8 mmol) was added slowly to a stirred solution of compound 1b (4.0 g, 13.4 mmol) and HATU (5.6 g, 14.7 mmol) in DMF (50 mL) and was allowed to stir at room temperature for 5 more min. To the above reaction mixture L-Ser($^t$Bu)-OMe.HCl (3.5 g, 20.1 mmol) was added slowly and stirred at room temperature for 12 h. The completeness of the reaction was confirmed by TLC analysis. The reaction mixture was quenched with ice, precipitated solid was filtered and re-crystallized with $CH_2Cl_2$ to yield 6 g of compound 1c, LCMS: 454.8 $(M+H)^+$.

Step 1c: 99% Hydrazine hydrate solution (10 mL) was added slowly to a stirred solution of compound 1c (6 g) in methanol (50 mL) and stirred at room temperature for 2 h. The completion of the reaction was confirmed by TLC. The reaction mixture on evaporation under reduced pressure yielded 5.8 g of compound 1d. LCMS: 455.0 $(M+H)^+$.

Step 1d: DIPEA (3.3 g, 25.4 mmol) was added slowly to a stirred solution of compound 1d (5.8 g, 12.7 mmol), HATU (5.8 g, 15.2 mmol) in DMF (50 mL) and was allowed to stir at room temperature for 5 min. Fmoc-L-Asn-OH (4.9 g, 14.0 mmol) was further added to reaction mixture and stirred at room temperature for 12 h. The completeness of the reaction was confirmed by TLC analysis. The reaction mixture was then quenched with ice, precipitated solid was filtered and re-crystallized with $CH_2Cl_2$ to yield 5.9 g of compound 1e, LCMS: 791.0 $(M+H)^+$.

Step 1e: Fmoc group of compound 1e [(5.9 g in $CH_2Cl_2$ (60 mL)] was deprotected using diethylamine (60 mL) and the completion of the reaction was confirmed by TLC analysis. The reaction mixture on evaporation under reduced pressure yielded 1.6 g of compound 1f. LCMS: 568.8 $(M+H)^+$.

Step 1f: Compound 11 (1.3 g, 3.0 mmol) and compound 1f (1.60 g, 2.8 mmol) was dissolved in THF (10 mL) and stirred at room temperature. Coupling was initiated by the addition of triethylamine (0.57 g, 5.6 mmol) to the above reaction mixture and the reaction was allowed to stir for 12 h at room temperature. The completeness of the reaction was confirmed by TLC analysis. Organic layer was washed with $NaHCO_3$, citric acid solution, brine, dried over $Na_2SO_4$ and evaporated under reduced pressure to yield 0.45 g of compound 1g.

Step 1g: Cbz group and benzyl ester deprotection was carried out on compound 1g (0.45 g) in methanol using palladium hydroxide (0.5 g) for 1 h at room temperature. The completeness of the reaction was confirmed by TLC analysis. Palladium hydroxide was removed by Celite® bed filtration and the filtrate was evaporated under reduced pressure to yield 0.34 g of compound 1h. LCMS: 636.0 $(M+H)^+$.

Step 1h: Cyclization of compound 1h (0.1 g, 0.15 mmol) was carried out using HOBT (0.06 g, 0.47 mmol) and PyBOP (0.24 g, 0.47 mmol) in THF (50 mL). The reaction was initiated by slow addition of DIPEA (0.06 g, 0.47 mmol) and further stirred at room temperature for 12 h. The reaction mixture was evaporated and washed with diethyl ether to yield 0.05 g of compound 1i. LCMS: 617.9 $(M+H)^+$.

Step 1i: The acid sensitive protecting group on compound 1i [(0.08 g) in $CH_2Cl_2$ (0.9 mL)] was removed using TFA (0.9 mL). The reaction mixture was stirred at room temperature for 4 h, followed by evaporation and washing with diethyl ether yielded 0.05 g of crude compound 1. The crude solid material was purified using preparative HPLC method-A described under experimental conditions (yield: 9 mg). LCMS: 506.4 $(M+H)^+$; HPLC: $t_R$=12.3 min.

Synthesis of compound 11 ($NO_2$—$C_6H_4$—OCO-Thr($^t$Bu)-OBzl,): To a solution of Fmoc-Thr($^t$Bu)-OH (15.0 g, 37.7 mmol) in 100.0 mL of DMF, $Cs_2CO_3$ (14.8 g, 45.2 mmol) was added and the resulting mixture was cooled to 0° C. To the cooled reaction mixture benzyl bromide (7.74 g, 345.2 mmol) was added and the solution was stirred for 30 min at ice cold temperature followed by room temperature for 12 h. The reaction mixture was further concentrated under reduced pressure and diluted with ethyl acetate (150 mL). The organic layer was washed with water (2×100 mL), brine (1×100 mL) and dried over $Na_2SO_4$. The filtered solution was concentrated and purified by silica gel column chromatogrophy (Eluent: 0-30% ethyl acetate in Hexane) to yield 18.5 g of intermediate 1j as a white solid. LCMS: 433.1 $(M-O^tBu+H)^+$. Fmoc group on compound 1j (10.0 g, 20.5 mmol) in $CH_2Cl_2$ (40.0 mL) was deprotected by stirring it with diethylamine (40.0 mL) for 1 h at room temperature. The resulting solution was concentrated in vacuum and the thick-residue was purified by column chromatography over neutral alumina (Eluent: 0-50% ethyl acetate in hexane then 0-5% methanol in chloroform) to yield 3.5 g of intermediate 1k (Yield: 70%). LCMS: 266.5 $(M+H)^+$. TEA (1.2 g, 12.0 mmol) was added to a stirred solution of intermediate 1k (1.6 g, 6.0 mmol) in $CH_2Cl_2$ (30 mL). Solution of 4-nitrophenyl chloroformate (1.3 g, 6.6 mmol) in $CH_2Cl_2$ (10 mL) was added to the above stirred solution and the reaction was continued for 12 h at room temperature. The completion of the reaction was confirmed by TLC analysis After completion of reaction, the reaction mixture was diluted with $CH_2Cl_2$ (50 mL) and washed with 1.0 M of sodium bi sulphate (50 mL×2) and 1.0 M sodium carbonate (50 mL×2), dried over Na$_2$SO$_4$ and evaporated under reduced pressure to yield crude compound 1l, which was further purified by silica gel column chromatography (eluent: 0-20% ethyl acetate in hexane) to yield 0.8 g of compound 1l. $^1$H NMR (DMSO-d$_6$, 300 MHz): δ 1.04 (s, 9H), 1.16 (d, 3H), 4.11 (m, 1H), 5.11 (m, 3H), 6.91 (d, 2H), 7.40 (m, 5H), 8.10 (d, 2H), 8.26 (brs, 1H).

EXAMPLE 2

Synthesis of Compound 2

Figure 2A:
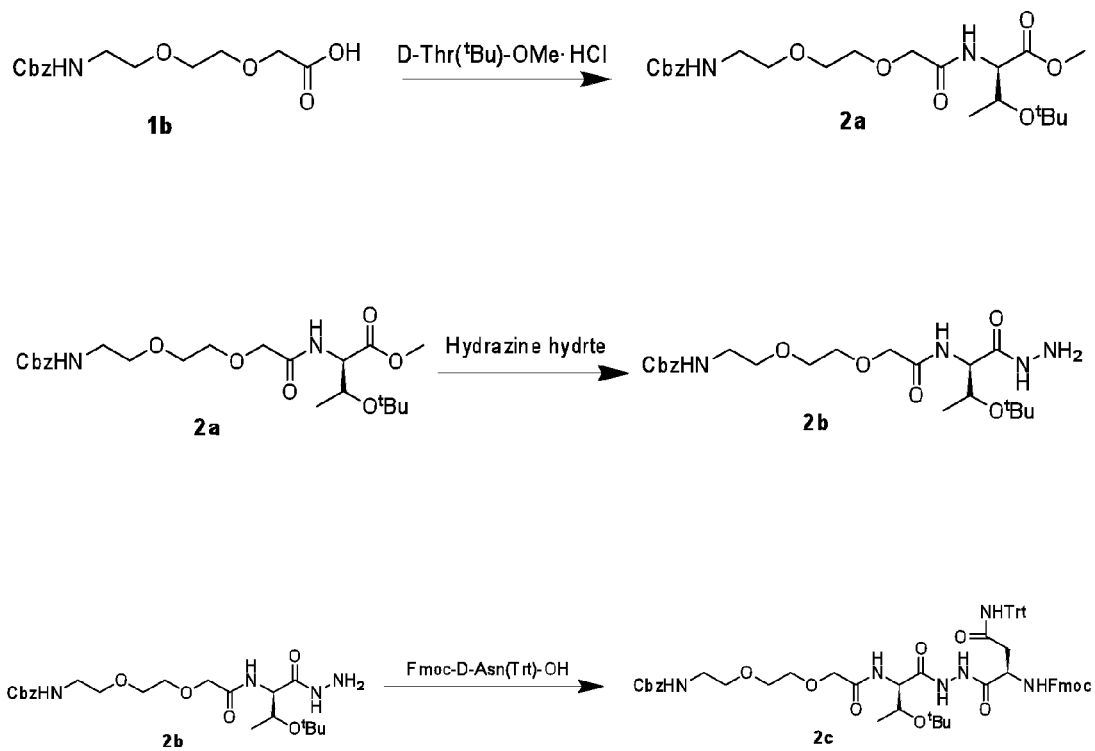
FIGS. 2A-2B depict the chemical synthetic scheme for Compound 2.
Figure 2B:
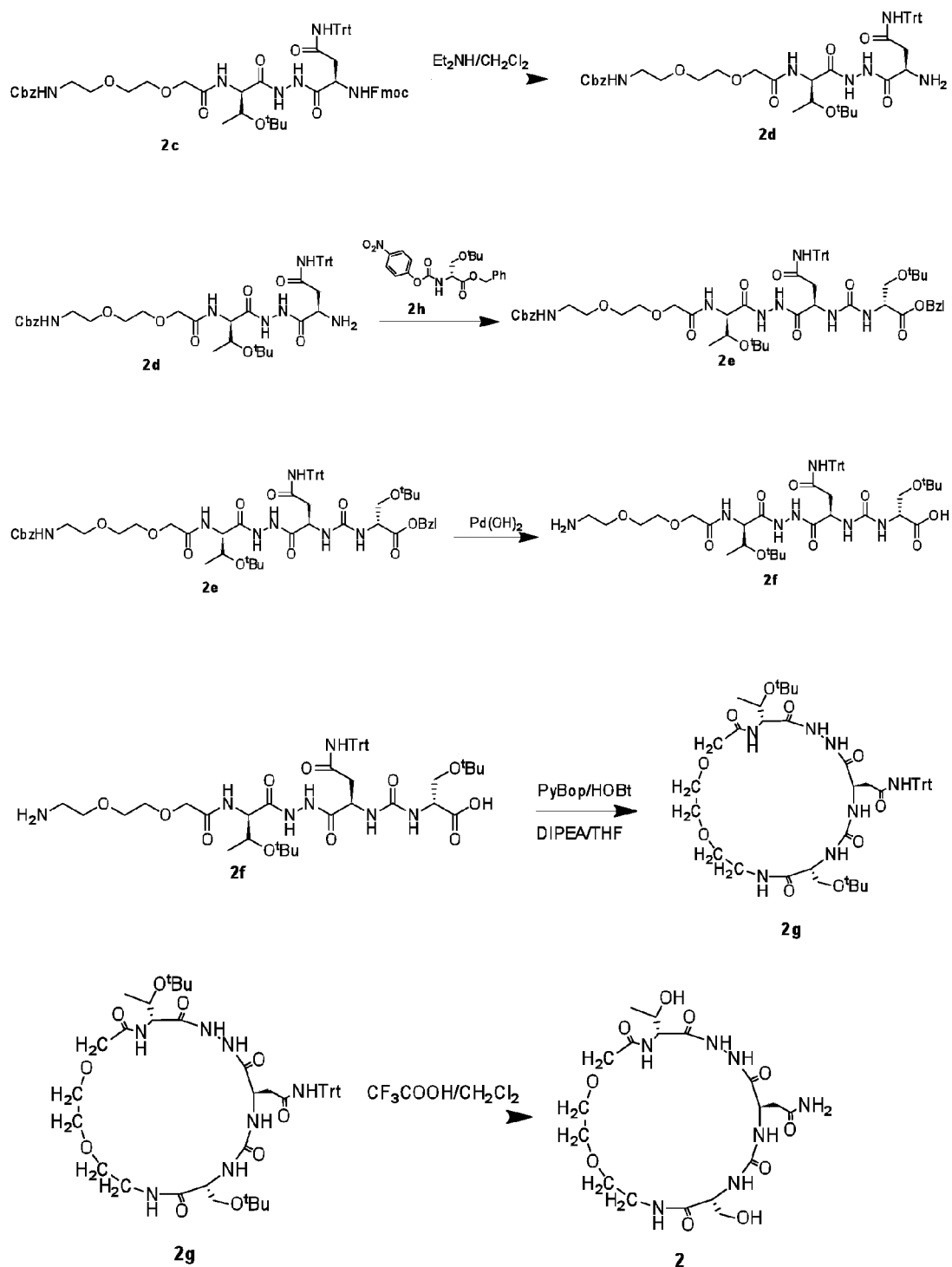

FIGS. 2A-2B illustrates Steps 2a and 2h.

Step 2a: DIPEA (2.71 g, 21 mmol) was added slowly to a stirred solution of compound 1b (3.12 g, 10.5 mmol), HATU (4.41 g, 11.6 mmol) in DMF (30 mL) and was allowed to stir at room temperature for 5 min. To the above reaction mixture D-Thr($^t$Bu)-OMe.HCl (2.0 g, 10.5 mmol) was added slowly and stirred at room temperature for 12 h. The completeness of the reaction was confirmed by TLC analysis. The reaction mixture was then quenched with ice, precipitate was filtered and re-crystallized with CH$_2$Cl$_2$ to yield 4.2 g of compound 2a. LCMS: 491.2 (M+Na)$^+$.

Step 2b: 99% Hydrazine hydrate solution (5 mL) was added slowly to a stirred solution of compound 2a (4.2 g) in methanol (40 mL) and the completion of the reaction was confirmed by TLC analysis. The reaction mixture on evaporation under reduced pressure yielded 4.2 g of compound 2b (Yield: 90%). LCMS: 469.4 (M+H)$^+$.

Step 2c: DIPEA (2.7 mL, 20.9 mmol) was added slowly to a stirred solution of compound 2b (4.9 g, 10.5 mmol), HATU (4.8 g, 12.5 mmol) in DMF (50 mL). To the above stirred solution, Fmoc-D-Asn(Trt)-OH (6.2 g, 10.5 mmol) was added and further stirred at room temperature for 12 h. The completeness of the reaction was confirmed by TLC analysis. The reaction mixture was diluted with EtOAc (30 mL) and washed with 1.0 M sodium carbonate (20 mL×2), 10% citric acid (20 mL×2), water (20 mL×2), dried over Na$_2$SO$_4$ and evaporated under reduced pressure to yield 10 g of crude intermediate 2c and was further purified by silica gel column chromatography (eluent: 0-5% MeOH in EtOAc) to yield 5 g of compound 2c. LCMS: 1047.7 (M+H)$^+$.

Step 2d: Fmoc deprotection of compound 2c [(3.2 g) in CH$_2$Cl$_2$ (10 mL)] was carried out using diethylamine (10 mL). The completion of the reaction was confirmed by TLC analysis. The resulting solution on evaporation under reduced pressure yielded 1.2 g of compound 2d.

Step 2e: Triethylamine (0.32 g, 3.2 mmol) was added slowly to initiate the coupling of compound 2d (1.3 g, 1.6 mmol) and compound 2h (0.79 g, 1.9 mmol) in THF (20 mL). The resulting solution was further allowed to stir for 12 h at room temperature and completeness of the reaction was confirmed by TLC analysis. Organic layer was washed with NaHCO$_3$, citric acid solution, brine, dried over Na$_2$SO$_4$ and evaporated under reduced pressure to yield 1.3 g of compound 2e.

Step 2f: Cbz group and benzyl ester deprotection was carried out on compound 2e (1.3 g) in methanol using palladium hydroxide (1.0 g) for 1 h at room temperature. The completeness of the reaction was confirmed by TLC analysis. Palladium hydroxide was removed by Celite® bed filtration and the filtrate was evaporated under reduced pressure to yield 0.45 g of compound 2f. LCMS: 878.4 (M+H)$^+$.

Step 2g: DIPEA (0.2 g, 1.5 mmol) was added slowly to a stirred solution of compound 2f (0.45 g, 0.51 mmol), HOBT (0.21 g, 1.53 mmol) and PyBOP (0.8 g, 1.53 mmol) in THF (200 mL). The reaction mixture was further stirred at room temperature for 12 h. The completeness of the reaction was confirmed by TLC analysis. The reaction mixture was evaporated and washed with diethyl ether to yield 0.41 g of intermediate 2g. LCMS: 860.7 (M+H)$^+$.

Step 2h: To a solution of compound 2g (0.4 g) in CH$_2$Cl$_2$ (5 mL), trifluoroacetic acid (5 mL) and catalytic amount of triisopropylsilane were added and stirred for 3 h at room temperature. The resulting solution was concentrated in vacuum to yield 0.2 g of crude compound 2. The crude solid material was purified (yield: 10 mg,) using preparative HPLC method-B described under experimental conditions. LCMS: 506.6 (M+H)$^+$; HPLC: t$_R$=12.4 min.

Synthesis of compound 2h (NO$_2$—C$_6$H$_4$—OCO-D-Ser($^t$Bu)-OBzl)

The compound was synthesised using similar procedure as exemplified in (example 1, compound 1l) using Fmoc-D-Ser($^t$Bu)-OH instead of Fmoc-Thr($^t$Bu)-OH to yield 1 g crude material of 2h.

EXAMPLE 3

Synthesis of Compound 3

Figure 3A:
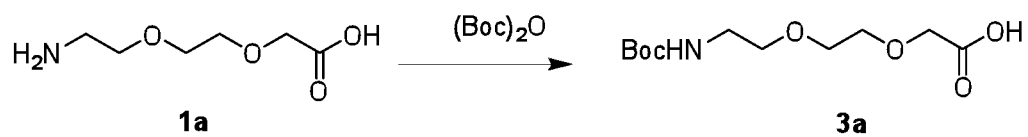
FIGS. 3A-3C depict the chemical synthetic scheme for Compound 3.
Figure 3A:
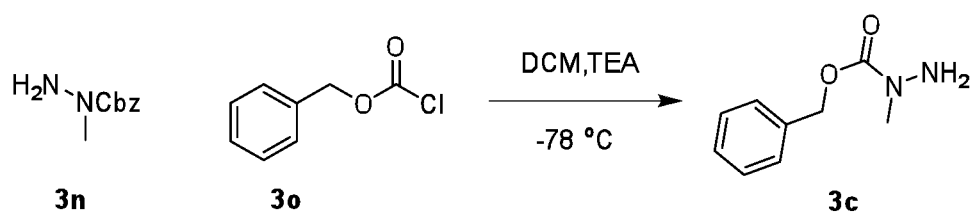
Figure 3A:
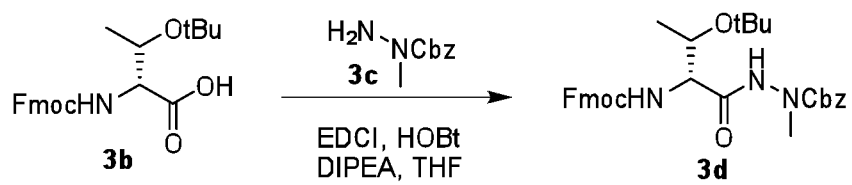
Figure 3A:
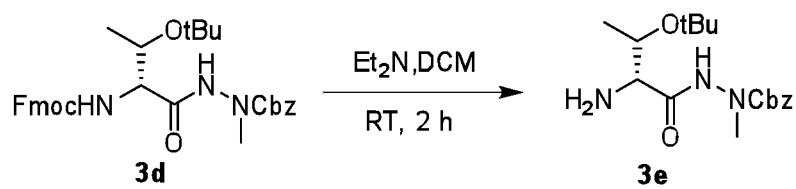
Figure 3A:
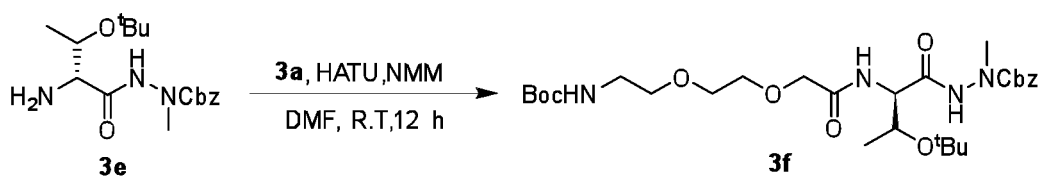
Figure 3B:
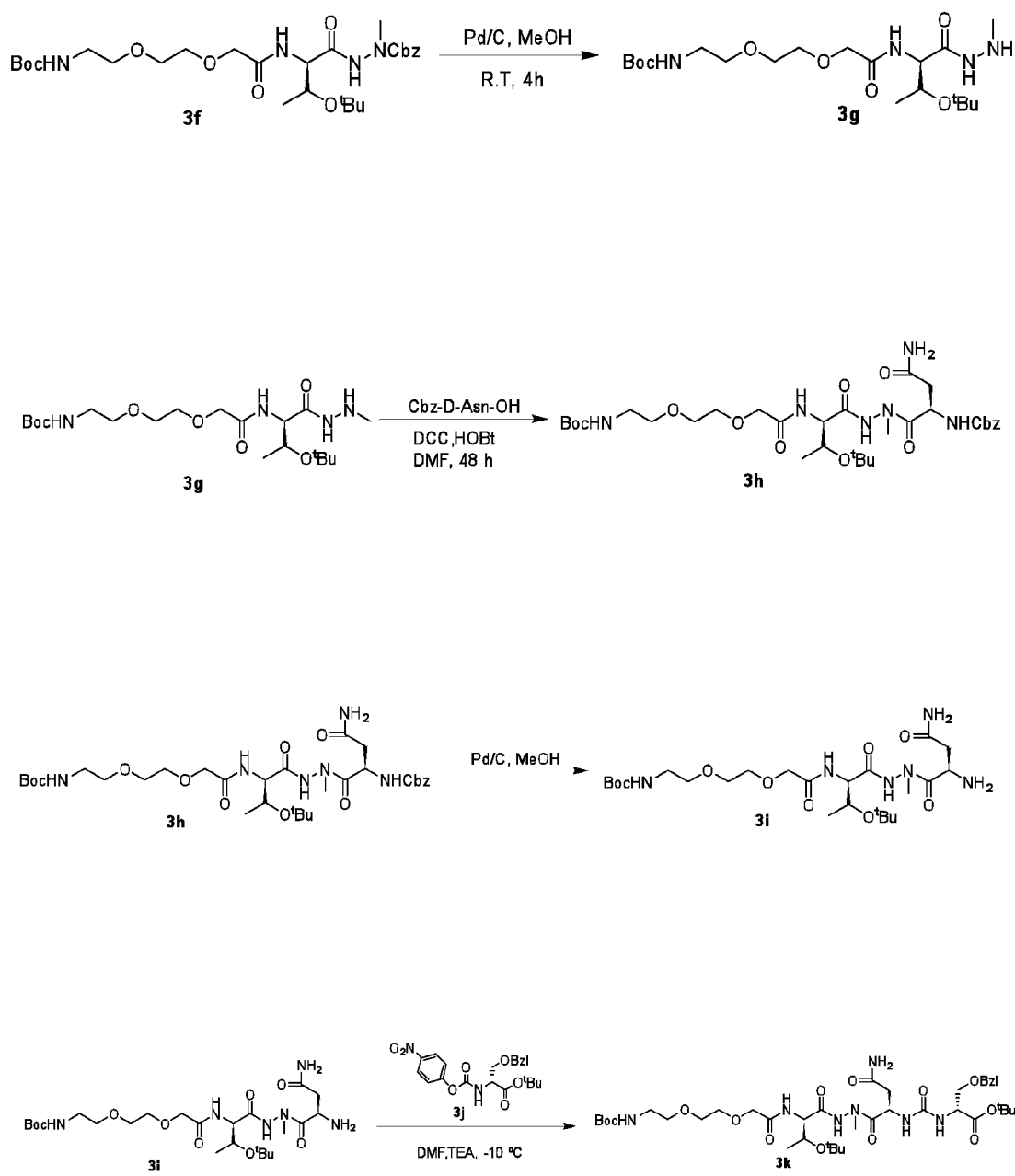
Figure 3C:
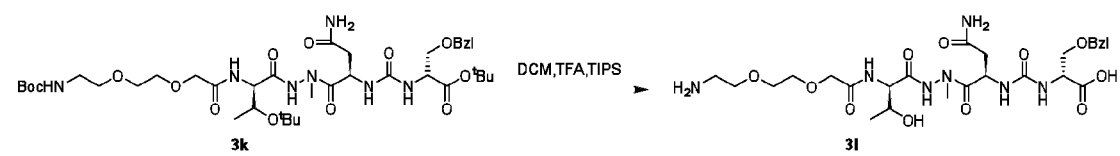
Figure 3C:
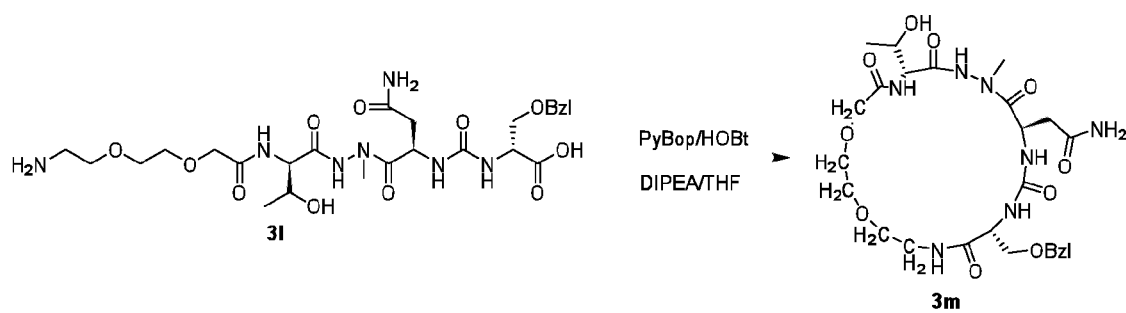
Figure 3C:
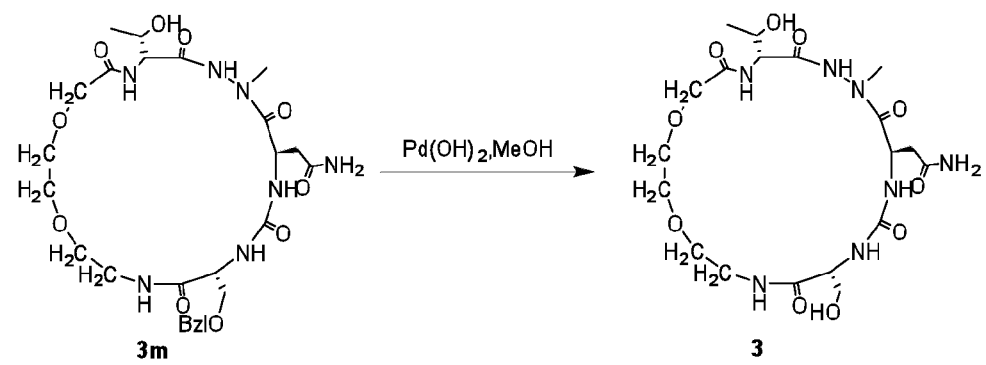

FIGS. 3A-3C illustrates Steps 3a and 3k.

Step 3a: To a stirred solution of compound 1a (5.0 g, 30.6 mmol) in 1,4-Dioxane (50 mL), Sodium carbonate (8.12 g, 76.5 mmol, dissolved in 10 mL water) and (Boc)$_2$O (9.98 mL, 45.7 mmol) were added and stirred at room temperature for 12 h. The progress of reaction was monitored by TLC. The reaction mass was partitioned between diethyl ether and water. Then aqueous layer was made acidic (pH=3) by 3N HCl solution and was extracted with DCM (2×200 mL). Organic layer was washed with water, brine, dried over Na$_2$SO$_4$ and evaporated under reduced pressure to yield 50 g of pure 3a (Yield: 62.1%). LCMS: 263.0 (M+H)$^+$.

Step 3b: DIPEA (6.5 mL, 37.8 mmol) was added slowly to a stirred solution of compound 3b (5 g, 12.6 mmol), compound 3c (2.72 g, 15 mmol), HOBt (2.55 g, 18.9 mmol) and EDC.HCl (3.62 g, 18.9 mmol) in DMF (75 mL) at 0° C. The reaction mixture was further stirred at room temperature for 12 h. The progress of the reaction was confirmed by TLC analysis. The reaction mass was partitioned between ethyl acetate and water. Organic layer was washed with water, brine, dried over Na$_2$SO$_4$ and evaporated under reduced pressure to yield crude. The crude compound was purified by silica gel (60-120 mesh) column chromatography using hexane/ethyl acetate (40:60) as elute to yield 5.2 g of compound 3d, (Yield: 71.0%). LCMS: 560.6 (M+H)$^+$.

Step 3c: To a stirred solution of compound 3d (5 g, 8.9 mmol) in dry DCM, diethylamine (50 mL) was added dropwise at −10° C. and stirred for 1 h at room temperature. After completion of reaction, the mixture was evaporated under reduced pressure to give crude compound. The crude was purified with (1:1) n-pentane/diethyl ether wash and dried under high vacuum to yield 3.5 g of compound 3e. LCMS: 338.58 (M+H)$^+$.

Step 3d: NMM (1.4 mL, 14.0 mmol) was added slowly to a stirred solution of compound 3a (3 g, 11.3 mmol), compound 3e (4.3 g, 12.9 mmol) and HATU (6.5 g, 17.1 mmol) in DMF (75 mL) at 0° C. The reaction mixture was further stirred for 6 h at room temperature. Progress of reaction was monitored by TLC. After completion, the reaction mass was partitioned between ethyl acetate and water. Organic layer was washed with water, brine, dried over Na$_2$SO$_4$ and evaporated under reduced pressure to give crude compound. The crude was purified by silica gel column chromatography (Eluent: 50% hexane in ethyl acetate) to yield 4.8 g of compound 3f, LCMS: 583.7 (M+H)$^+$.

Step 3e: To a stirred solution of compound 3f (4.5 g, 7.7 mmol) in MeOH, Pd/C (2.0 g) was added slowly and stirred under H$_2$ atmosphere for 4 h at room temperature. Progress of reaction was monitored by TLC. After completion, the reaction mass was filtered through Celite® and washed with MeOH (2×150 mL). The resulting filtrate was evaporated under reduced pressure to yield 3 g of compound 3g LCMS: 448.6 (M+H)$^+$.

Step 3f: To a stirred solution of Cbz-D-Asn-OH (1.78 g, 6.7 mmol) and compound 3g (3.0 g, 6.8 mmol) in DMF (75 mL), DCC (4.12 g, 20.3 mmol) and HOBT (1.8 g, 13.5 mmol) were added slowly at 0° C. The reaction mixture was stirred for 48 h at room temperature. Progress of reaction was monitored by TLC. After completion, the reaction mass was partitioned between ethyl acetate and water. Organic layer was washed with water, brine, dried over Na$_2$SO$_4$ and evaporated under reduced pressure to yield crude. The crude compound was purified by silica gel (60-120 mesh) column chromatography (Eluent: 4% MeOH in DCM) to yield 2.5 g of Compound 3h, LCMS: 697.50 (M+H)$^+$.

Step 3g: To a stirred solution of compound 3h (2.5 g, 3.6 mmol) in MeOH (50 mL), Pd/C (1.2 g) was added and stirred under H$_2$ atmosphere for 4 h at room temperature. Progress of reaction was monitored by TLC. After completion, the reaction mass was filtered through Celite® and washed with MeOH (2×150 mL). The resulting filtrate was evaporated under reduced pressure to yield 1.5 g of compound 3i, LCMS: 563.6 (M+H)$^+$.

Step 3h: Compound 3i (1.3 g, 2.3 mmol), TEA (0.43 mL, 3.5 mmol) in DMF (25 mL) and was added dropwise slowly to a solution of 3j (1.1 g, 2.6 mmol) at −10° C. The mixture was further stirred at room temperature for 2 h. Progress of reaction was monitored by TLC. After completion, the reaction mass was partitioned between ethyl acetate and water. Organic layer was washed with NaHCO$_3$, citric acid solution, brine, then organic layer was dried over Na$_2$SO$_4$ and evaporated under reduced pressure to give crude. The crude was purified by silica gel (60-120 mesh) column chromatography (hexane/ethyl acetate (10:90) as elute) to yield 1.2 g of compound 3k. LCMS: 840.6 (M+H)$^+$.

Step 3i: To a solution of compound 3k (1.0 g, 1.2 mmol) in CH$_2$Cl$_2$ (10 mL), trifluoroacetic acid (10 mL) and catalytic amount of triisopropylsilane were added and stirred for 3 h at room temperature to remove the acid sensitive protecting groups. The resulting solution was concentrated in vacuum and washed with diethyl ether to afford 1.0 g of crude compound 3l, LCMS: 628.65 (M+H)$^+$.

Step 3j: To a stirred solution of compound 3l (1.0 g, 1.5 mmol) in THF, PyBOP (2.4 g, 4.7 mmol), HOBT (0.6, 4.7 mmol) and DIPEA (0.8 mL, 4.7 mmol) were added slowly and stirred for 12 h at room temperature. The reaction mass was partitioned between water and ethyl acetate. Organic layer was washed with water, brine, dried over Na$_2$SO$_4$ and evaporated under reduced pressure to give crude. Crude compound was washed with diethyl ether to yield 0.8 g of compound 3m, LCMS: 610.5 (M+H)$^+$.

Step 3k: To a stirred solution of compound 3m (0.8 g, 1.3 mmol) in MeOH (30 mL), Pd(OH)$_2$ (0.4 g) was added and stirred under H$_2$ atmosphere for 4 h at room temperature. Progress of reaction was monitored by TLC. After completion, the reaction mass was filtered through Celite® and washed with MeOH (2×150 mL). The resulting filtrate was evaporated under reduced pressure to yield 0.7 g of compound 3. LCMS: 520.5 (M+H)$^+$; HPLC: $t_R$=9.9 min.

Synthesis of Intermediate 3c: To a stirred solution of compound 3n (4 g, 88.3 mmol) and compound 3o (10.2 mL, 71.2 mmol) in DCM (150 mL), TEA (14.4 mL, 105 mmol) was added dropwise at −78° C. The reaction mixture was allowed to attain room temperature and stirred for 12 h. Progress of reaction was monitored by TLC. After completion, the reaction mass was partitioned between water and DCM. Organic layer was washed with water, brine, dried over Na$_2$SO$_4$ and evaporated under reduced pressure to yield crude compound and was purified by silica gel (60-120 mesh) column chromatography (Eluent: 80% ethyl acetate in hexane) to yield 10 g of Compound 3c, LCMS: 181.18 (M+H)$^+$.

Synthesis of 3j (NO$_2$—C$_6$H$_4$—OCO-D-Ser(Bzl)-O$^t$Bu): The compound was synthesised using similar procedure as exemplified in (example 1, compound 1k) using Fmoc-D-Ser(Bzl)-O$^t$Bu instead of Fmoc-Thr($^t$Bu)-OH to yield 1.5 g of compound 3j.

EXAMPLE 4

Synthesis of Compound 4

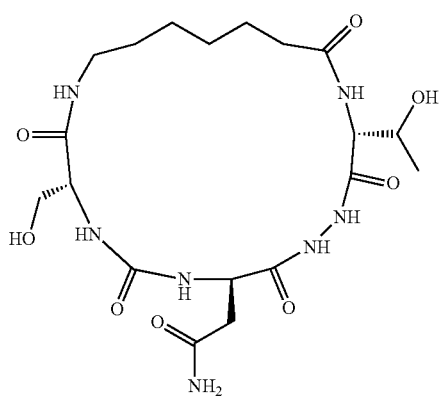 [SMILES: CC(O)[C@H]1NC(=O)CCCCCCNC(=O)[C@@H](CO)NC(=O)N[C@H](CC(N)=O)C(=O)NNC1=O]

The compound was synthesised using a similar procedure as depicted in Example 2 (compound 2) using 7-aminoheptanoic acid instead compound 1a to yield 0.3 g crude material of the title compound. The crude solid material was purified using preparative HPLC described under experimental conditions. LCMS: 488.2 (M+H)$^+$; HPLC: $t_R$=11.9 min.

The compounds in Table 3 below were prepared based on the synthetic procedures described above.

TABLE 3

| Compound No. | Structure | LCMS (M + H)+ | HPLC (t_R in min.) |
|---|---|---|---|
| 5 | 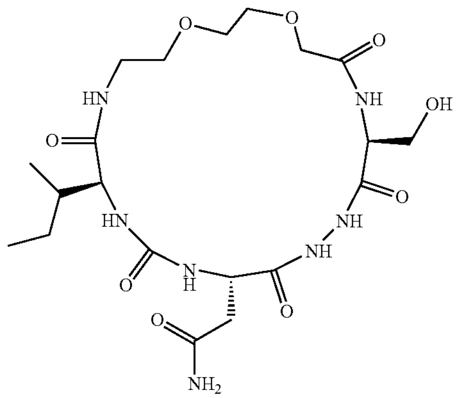 [SMILES: CCC(C)[C@@H]1NC(=O)N[C@@H](CC(N)=O)C(=O)NNC(=O)[C@H](CO)NC(=O)COCCOCCNC1=O] | 518.2 | 9.7 |
| 6 | 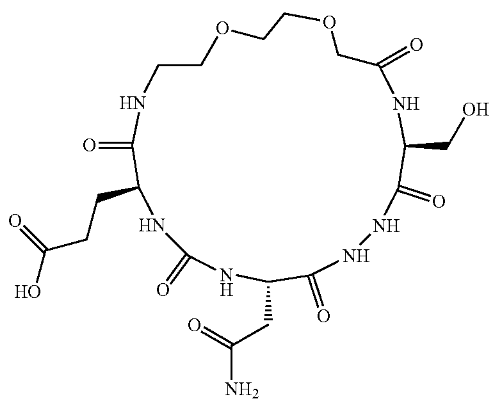 [SMILES: NC(=O)C[C@@H]1NC(=O)N[C@@H](CCC(=O)O)C(=O)NCCOCCOCC(=O)N[C@@H](CO)C(=O)NNC1=O] | 534.2 | 12.4 |
| 7 | 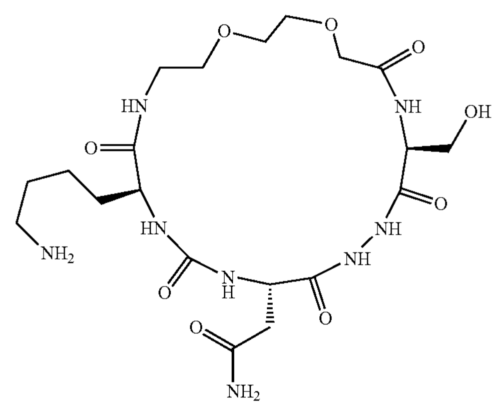 [SMILES: NCCCC[C@@H]1NC(=O)N[C@@H](CC(N)=O)C(=O)NNC(=O)[C@H](CO)NC(=O)COCCOCCNC1=O] | 532.9 | — |
| 8 | 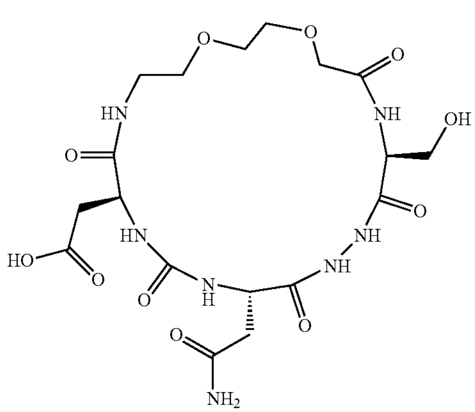 [SMILES: NC(=O)C[C@@H]1NC(=O)N[C@@H](CC(=O)O)C(=O)NCCOCCOCC(=O)N[C@@H](CO)C(=O)NNC1=O] | 520.2 | 9.03 |

TABLE 3-continued
| Compound No. | Structure | LCMS (M + H)+ | HPLC (t$_R$ in min.) |
|---|---|---|---|
| 9 | 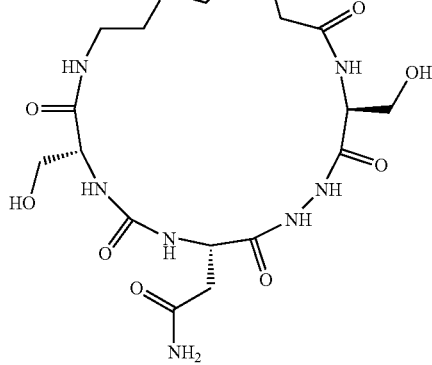 | 492.1 | 12.9 |
| 10 | 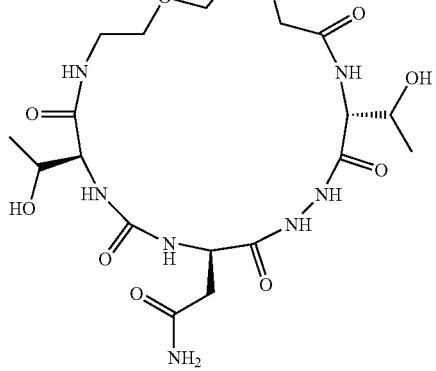 | 520.2 | 11.23 |
| 11 | 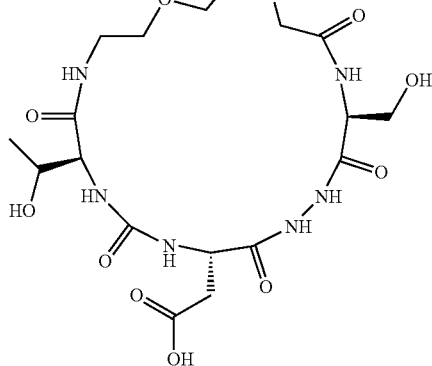 | 507.2 | 11.96 |

TABLE 3-continued

| Compound No. | Structure | LCMS (M + H)+ | HPLC (t_R in min.) |
|---|---|---|---|
| 12 | 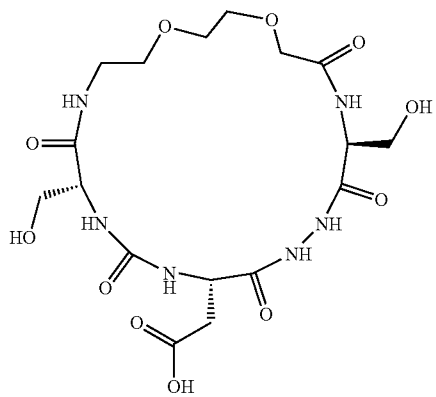 [SMILES: O=C(O)C[C@@H]1NC(=O)N[C@H](CO)C(=O)NCCOCCOCC(=O)N[C@@H](CO)C(=O)NNC1=O] | 493.2 | 8.35 |
| 13 | 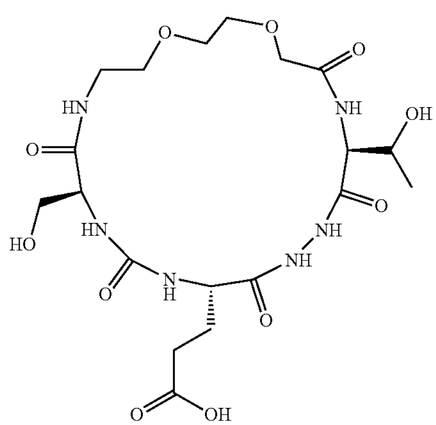 [SMILES: CC(O)[C@@H]1NC(=O)COCCOCCNC(=O)[C@H](CO)NC(=O)N[C@@H](CCC(=O)O)C(=O)NNC1=O] | 521.3 | 12.2 |
| 14 | 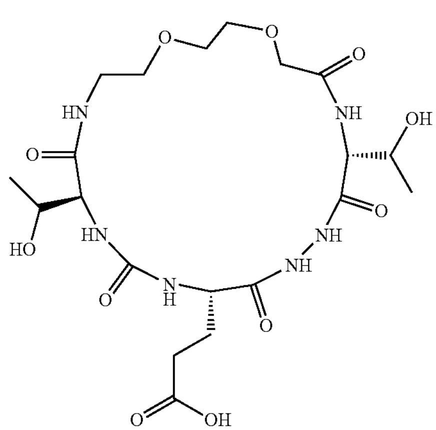 [SMILES: CC(O)[C@@H]1NC(=O)N[C@@H](CCC(=O)O)C(=O)NNC(=O)[C@@H](C(C)O)NC(=O)COCCOCCNC1=O] | 535.4 | 11.2 |

The compounds shown in below Table 4, which can be prepared by following similar procedure as described above with suitable modification known to the one ordinary skilled in the art are also included in the scope of the present application.

TABLE 4

| Compound No. | Structure |
| --- | --- |
| 15 | 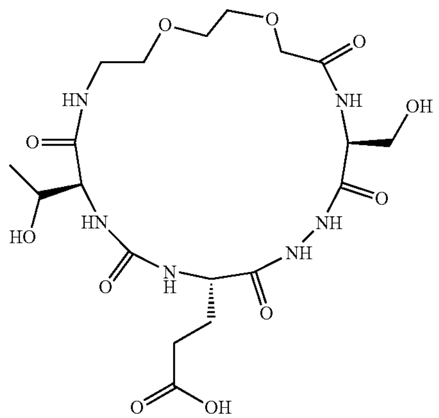 [SMILES: CC(O)[C@@H]1NC(=O)N[C@@H](CCC(=O)O)C(=O)NNC(=O)[C@H](CO)NC(=O)COCCOCCNC1=O] |
| 16 | 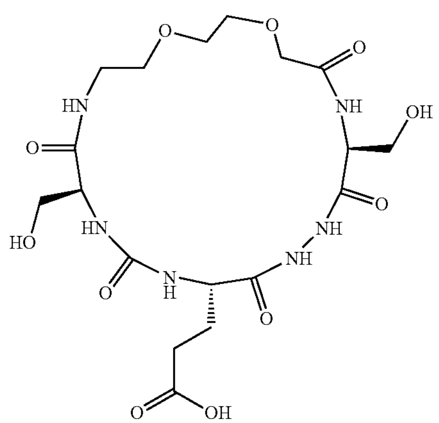 [SMILES: O=C(O)CC[C@@H]1NC(=O)N[C@@H](CO)C(=O)NCCOCCOCC(=O)N[C@@H](CO)C(=O)NNC1=O] |
| 17 | 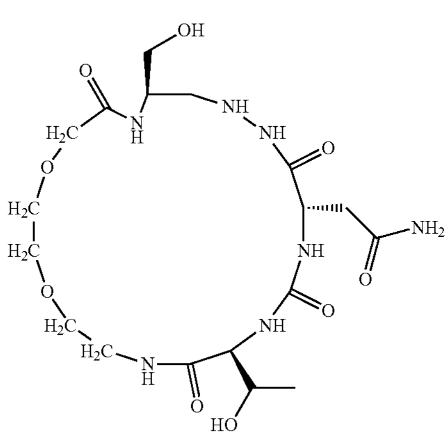 [SMILES: CC(O)[C@@H]1NC(=O)N[C@@H](CC(N)=O)C(=O)NNC[C@H](CO)NC(=O)COCCOCCNC1=O] |

TABLE 4-continued

| Compound No. | Structure |
| --- | --- |
| 18 | 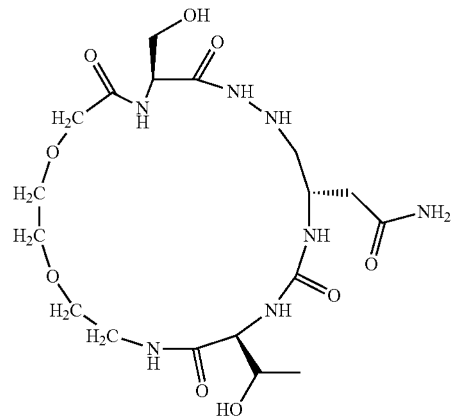 [SMILES: CC(O)[C@@H]1NC(=O)N[C@@H](CC(N)=O)CNNC(=O)[C@H](CO)NC(=O)COCCOCCNC1=O] |
| 19 | 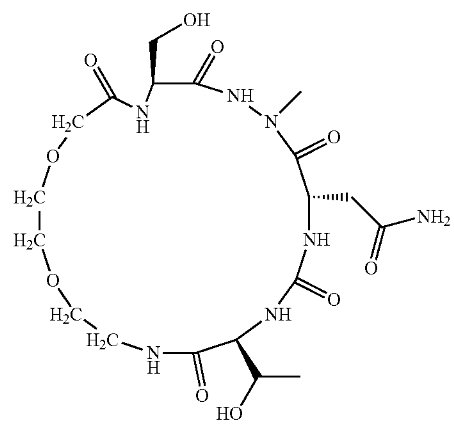 [SMILES: CC(O)[C@@H]1NC(=O)N[C@@H](CC(N)=O)C(=O)N(C)NC(=O)[C@H](CO)NC(=O)COCCOCCNC1=O] |
| 20 | 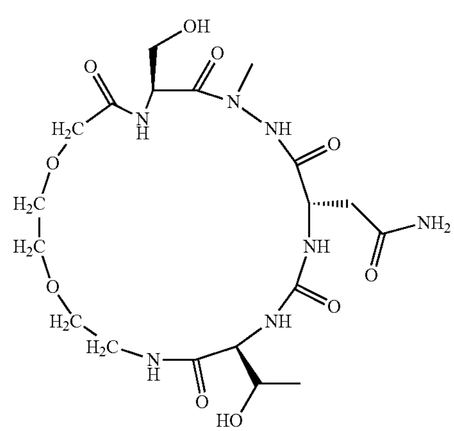 [SMILES: CC(O)[C@@H]1NC(=O)N[C@@H](CC(N)=O)C(=O)NN(C)C(=O)[C@H](CO)NC(=O)COCCOCCNC1=O] |

TABLE 4-continued

| Compound No. | Structure |
|---|---|
| 21 | (structure) |
| 22 | (structure) |
| 23 | (structure) |
| 24 | (structure) and |
| 25 | (structure) |

EXAMPLE 5

Rescue of Mouse Splenocyte Proliferation in the Presence of Recombinant PD-L1

Recombinant mouse PD-L1 (rm-PDL-1, cat no: 1019-B7-100; R&D Systems) were used as the source of PD-L1.

Requirement:

Mouse splenocytes harvested from 6-8 weeks old C57 BL6 mice; RPMI 1640 (GIBCO, Cat #11875); DMEM with high glucose (GIBCO, Cat # D6429); Fetal Bovine Serum [Hyclone, Cat # SH30071.03]; Penicillin (10000 unit/ml)-Streptomycin (10,000 μg/ml) Liquid (GIBCO, Cat #15140-122); MEM Sodium Pyruvate solution 100 mM (100×), Liquid (GIBCO, Cat #11360); Nonessential amino acid (GIBCO, Cat #11140); L-Glutamine (GIBCO, Cat #25030); Anti-CD3 antibody (eBiosciences—16-0032); Anti-CD28 antibody (eBiosciences—16-0281); ACK lysis buffer (1 mL) (GIBCO, Cat #-A10492); Histopaque (density-1.083 gm/mL) (SIGMA 10831); Trypan blue solution (SIGMA-T8154); 2 mL Norm Ject Luer Lock syringe-(Sigma 2014-12); 40 μm nylon cell strainer (BD FALCON 35230); Hemacytometer (Bright line-SIGMA Z359629); FACS Buffer (PBS/0.1% A BSA): Phosphate Buffered Saline (PBS) pH 7.2 (HiMedia TS1006) with 0.1% Bovine Serum Albumin (BSA) (SIGMA A7050) and sodium azide (SIGMA 08591); 5 mM stock solution of CFSE: CFSE stock solution was prepared by diluting lyophilized CFSE with 180 μL of Dimethyl sulfoxide (DMSO $C_2H_6SO$, SIGMA-D-5879) and aliquoted in to tubes for further use. Working concentrations were titrated from 10 μm to 1 μm. (eBioscience-650850-85); 0.05% Trypsin and 0.02% EDTA (SIGMA 59417C); 96-well format ELISA plates (Corning CLS3390); BD FACS caliber (E6016); Recombinant mouse B7-H1/PDL1 Fc Chimera, (rm-PD-L1 cat no: 1019-B7-100).

Protocol

Splenocyte preparation and culturing:

Splenocytes harvested in a 50 mL falcon tube by mashing mouse spleen in a 40 μm cell strainer were further treated with 1 ml ACK lysis buffer for 5 mins at room temperature. After washing with 9 mL of RPMI complete media, cells were re-suspended in 3 ml of 1×PBS in a 15 mL tube. 3 mL of Histopaque was added carefully to the bottom of the tube without disturbing overlaying splenocyte suspension. After centrifuging at 800×g for 20 min. at room temperature, the opaque layer of splenocytes was collected carefully without disturbing/mixing the layers. Splenocytes were washed twice with cold 1×PBS followed by total cell counting using Trypan Blue exclusion method and used further for cell based assays.

Splenocytes were cultured in RPMI complete media (RPMI+10% fetal bovine serum+1 mM sodium pyruvate+10,000 units/mL penicillin and 10,000 μg/mL streptomycin) and maintained in a $CO_2$ incubator with 5% $CO_2$ at 37° C.

CFSE Proliferation Assay:

CFSE is a dye that passively diffuses into cells and binds to intracellular proteins. $1 \times 10^6$ cells/ml of harvested splenocytes were treated with 5 μm of CFSE in pre-warmed 1×PBS/0.1% BSA solution for 10 mins at 37° C. Excess CFSE was quenched using 5 volumes of ice-cold culture media to the cells and incubated on ice for 5 min. CFSE labelled splenocytes were further given three washes with ice cold complete RPMI media. CFSE labelled $1 \times 10^5$ splenocytes added to wells containing either MDA-MB231 cells ($1 \times 10^5$ cells cultured in high glucose DMEM medium) or recombinant human PDL-1 (100 ng/mL) and test compounds. Splenocytes were stimulated with anti-mouse CD3 and anti-mouse CD28 antibody (1 μg/mL each), and the culture was further incubated for 72 h at 37° C. with 5% $CO_2$. Cells were harvested and washed thrice with ice cold FACS buffer and % proliferation was analysed by flow cytometry with 488 nm excitation and 521 nm emission filters.

Data Compilation, Processing and Inference:

Percent splenocyte proliferation was analysed using cell quest FACS program and percent rescue of splenocyte proliferation by compound was estimated after deduction of % background proliferation value and normalising to % stimulated splenocyte proliferation (positive control) as 100%.

Background proliferation: Splenocytes+anti-CD3/CD28+PD-L1

Stimulated splenocytes: Splenocytes+anti-CD3/CD28 stimulation

Compound proliferation: Splenocytes+anti-CD3/CD28+PD-L1+Compound

Compound effect is examined by adding required conc. of compound to anti-CD3/CD28 stimulated splenocytes in presence of ligand (PDL-1)

Table 5 shows the rescue of mouse splenocyte proliferation inhibited by recombinant mouse PDL1 using CFSE based assay:

TABLE 5

| Compound No. | Percent rescue of splenocyte proliferation @ 100 nM compound concentration |
| --- | --- |
| 1 | 95 |
| 2 | 94 |
| 3 | 58 |
| 4 | 49 |
| 5 | 53 |
| 8 | 68 |
| 9 | 73 |
| 10 | 89 |
| 12 | 91 |

What is claimed is:

1. A method of making a compound according to the following scheme:

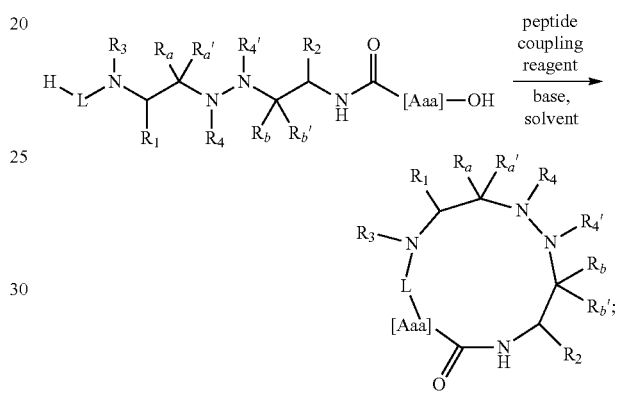

wherein:
R$_1$ is a side chain of an amino acid residue selected from Ala, Ser, Thr and Leu;
R$_2$ is a side chain of an amino acid residue selected from Asp, Glu, Gln and Asn;
[Aaa] is an amino acid residue selected from Ser, Asp, Ala, Ile, Phe, Trp, Lys, Glu and Thr;
R$_3$ is hydrogen or alkyl;
each of R$_4$ and R$_4$' independently is hydrogen or alkyl;
both R$_a$ and R$_a$' are hydrogen; or together are an oxo(=O) group;
both R$_b$ and R$_b$' are hydrogen; or together are an oxo (=O) group;
L is

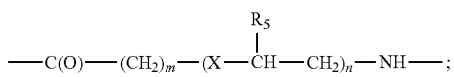

X is CH$_2$, O or S;
R$_5$ is hydrogen or alkyl;
m is an integer from 1 to 3; and
n is an integer from 2 to 20.

2. The method of claim 1, wherein [Aaa] is an amino acid residue selected from Ser or Thr.

3. The method of claim 1, wherein R$_1$ is the side chain of the amino acid residue Ser or Thr.

4. The method of claim 1, wherein the base is diisopropylethylamine.

5. The method of claim 1, wherein the solvent is tetrahydrofuran.

6. The method of claim 1, wherein the peptide coupling agent is benzotriazol-1-yl-oxytripyrrolidinophosphonium hexafluorophosphate (PyBOP).

* * * * *